United States Patent [19]

Fox, Jr. et al.

[11] Patent Number: 5,616,338

[45] Date of Patent: Apr. 1, 1997

[54] INFECTION-RESISTANT COMPOSITIONS, MEDICAL DEVICES AND SURFACES AND METHODS FOR PREPARING AND USING SAME

[75] Inventors: Charles L. Fox, Jr., New York, N.Y.; Shanta M. Modak, River Edge, N.J.; Lester A. Sampath, Nyack, N.Y.

[73] Assignee: Trustees of Columbia University in The City of New York, New York, N.Y.

[21] Appl. No.: 687,844

[22] Filed: Apr. 19, 1991

Related U.S. Application Data

[63] Continuation of Ser. No. 258,189, Oct. 14, 1988, Pat. No. 5,019,096, which is a continuation-in-part of Ser. No. 254,920, Feb. 11, 1988, abandoned.

[51] Int. Cl.$^6$ .................................................... A61F 2/02
[52] U.S. Cl. ................................................ 424/423; 523/112
[58] Field of Search ................................. 424/422, 423, 424/426; 523/112

[56] References Cited

U.S. PATENT DOCUMENTS

| | | |
|---|---|---|
| 3,705,938 | 12/1972 | Hyman et al. . |
| 4,381,380 | 4/1983 | LeVeen et al. . |
| 4,592,920 | 6/1986 | Murtfeldt . |
| 4,603,152 | 7/1986 | Laurin et al. . |
| 4,675,347 | 6/1987 | Mochizuki et al. . |
| 4,677,143 | 6/1987 | Laurin et al. . |
| 4,853,978 | 8/1989 | Stockum . |
| 4,925,668 | 5/1990 | Khan et al. ............................ 424/422 |

OTHER PUBLICATIONS

Solomon et al., J. Controlled Release (1987) pp. 343–352 "Antibiotic Realing Polymers".

Lazarus et al., J. Biomed. Mater. Res. (1971) vol. 5, pp. 129–138 "A Hydrophilic Polymer–Coated Antimicrobial Urethral Catheter".

Szycher, "Controlled Delivery of Topical Antibiotics", Novel Drug Delivery Technologies Conference pp. 13.1–13.14.

Bayston et al., J. Clin. Pathol. (1981) 198; 134 pp. 1057–1062 "Antimicrobial activity of silicone rubber used in hydrocephalus shunts . . . ".

Van Noort et al., J. Biomedical Materials Research, (1979) vol. 13, pp. 623–630 "Mechanical properties of antibacterial silicone rubber for hydrocephalus shunts".

Brook et al., Biomaterials, (1986) vol. 7, pp. 292–296 "Controlling drug release from acrylic polymers: In vitro studies . . . ".

Coventry et al., J. of Clinical Periodontology, (1982) vol. 9, pp. 129–133 "Experimental use of a slow release device employing chlorhexidine gluconate . . . ".

Tuominen et al., Annals of Clinical Research, (1981) vol. 13, pp. 425–528 "The effect of local antiseptic, chlorhexidine, in preventing infection . . . ".

Harper et al., Paraplegia, (1983) vol. 21, pp. 86–93 "Simple additives to increase the activity of chlorhexidine digluconate . . . ".

*Primary Examiner*—Carlos Azpuru
*Attorney, Agent, or Firm*—Brumbaugh, Graves, Donohue & Raymond

[57] ABSTRACT

A method of preparing an infection-resistant medical device comprising one or more matrix-forming polymers selected from the group consisting of biomedical polyurethane, biomedical silicones and biodegradable polymers, and antimicrobial agents, especially a synergistic combination of a silver salt and chlorhexidine (or its salts); also disclosed are medical devices having the synergistic composition therein or compositions thereon.

2 Claims, No Drawings

INFECTION-RESISTANT COMPOSITIONS, MEDICAL DEVICES AND SURFACES AND METHODS FOR PREPARING AND USING SAME

The present invention relates to infection-resistant compositions, medical devices and surfaces and to methods for using and preparing the same. This application is a continuation of U.S. patent applications 07/258,189 filed Oct. 14, 1988, now U.S. Pat. No. 5,019,096 which is a continuation-in-part of U.S. patent application Ser. No. 254,920, filed Feb. 11, 1988, now abandoned.

BACKGROUND OF THE INVENTION

Medical devices for use externally or internally with humans or animals can serve to introduce bacterial, viral, fungal or other undesirable infections. Certain prior art devices become unworkable after a short period of time, and must be replaced. In the case of urinary catheters, for example, frequent replacement can cause excessive discomfort to the patient and prolonged hospitalization. In the case of intravenous catheters used for critical care patients, infections can themselves prove life threatening. Additionally, there is always a threat of exposure to infectious contamination from surfaces that contact patients, from surgical gloves, and from other medical gear and apparatus.

To prevent such contamination, medical devices can be treated with an antimicrobial agent. Known methods of preparing an infection-resistant medical device have been proposed in U.S. Pat. Nos. 3,566,874, 3,674,901, 3,695,921, 3,705,938, 3,987,797, 4,024,871, 4,318,947, 4,381,380, 4,539,234, and 4,612,337.

In addition, antimicrobial compositions useful as coatings for medical devices or for forming the device itself are disclosed in U.S. Pat. Nos. 3,699,956, 4,054,139, 4,592,920, 4,603,152, and 4,667,143. However, such known methods are somewhat complicated or deficient in the results obtained. The art has great need for medical devices which are able to resist microbial infection when placed in the area of the body to which it is applied and which provide this resistance over the period of time which it remains in place. At the same time, these desirable characteristics must be achieved without sacrifice of other well recognized desirable characteristics. In the case of catheters, for example, it is important that any coating thereon leave a surface which provides a minimum of resistance to insertion of the catheter and which does not release a toxic substance to be adsorbed by the body.

Furthermore, some uses of antimicrobial metal compounds including silver salts in antimicrobial coatings for medical devices are known. Also, chlorhexidine and its salts are known to be powerful antiseptics, but the combination of chlorhexidine with silver nitrate has been shown to have prophylactic properties in burn therapy. In addition, the combination of chlorhexidine and sulfadiazine is known in topical applications to exhibit synergism against strains of Pseudomonas, Proteus, and Staphylococcus, as disclosed in Quesnel et al, *Synergism between Chlorhexidine and Sulphadiazine*, Journal of Applied Bacteriology, 1978, 45, 397–405.

SUMMARY OF THE INVENTION

A principal object of the present invention is to provide an improved method of preparing an infection-resistant medical device which will impart antimicrobial activity to the medical device through a sustained and controlled activity rate over an appreciable period of time, without hampering the biocompatibility of the surface and other intended functions of the device. A further object of the present invention is to provide an infection-resistant medical device having superior antimicrobial properties.

Still another object of the present invention is to provide an antimicrobial composition useful in providing an antimicrobial coating on medical devices.

In accordance with the first embodiment of the present invention, there is provided a method of preparing an infection-resistant medical device which comprises (a) preparing a coating vehicle by dissolving a matrix-forming polymer selected from the group consisting of biomedical polyurethane, biomedical silicones, biodegradable polymers and combinations thereof in at least one solvent therefor;

(b) incorporating at least one antimicrobial agent in the coating vehicle to form a coating composition;

(c) coating a medical device with the coating composition; and (d) drying the coated medical device.

It is preferred in the first embodiment that the antimicrobial agent be a combination of a silver salt and a biguanide and further preferred that the antimicrobial agent be a combination of a silver salt and a member of the group consisting of chlorhexidine and its salts. Also useful are chlorhexidine alone or in combination with nonoxynol 9, or pipracil as well as silver sulfadiazine in combination with nonoxynol 9.

In accordance with a second embodiment of the present invention, there is provided an antimicrobial composition comprising a mixture of (a) chlorhexidine and its salts, and (b) a silver salt.

Further, in accordance with a second embodiment of the present invention there is provided a method of preparing an infection-resistant medical device which comprises incorporating thereon or therein an antimicrobial agent comprising (a) a member of the group consisting of chlorhexidine and its salts, and (b) a member of the group consisting of silver and its salts.

The second embodiment of the present invention further provides an infection-resistant medical device having a coating thereon comprising (a) a member of the group consisting of chlorhexidine and its salts, and (b) a member of the group consisting of silver and its salts.

Another embodiment of the present invention still further provides a method for coating a medical device to provide an infection-resistant coating thereon which comprises the steps of:

(a) dissolving a matrix-forming polymer in a solvent therefor;

(b) dissolving an antimicrobial agent selected from the group consisting of chlorhexidine and its salts in a solvent which is miscible with the solvent polymer mixture prepared in step (a);

(c) dispersing a silver salt in one of the solutions prepared in (a) or (b);

(d) combining the solvent solutions and dispersions prepared in steps (a), (b) and (c) to provide a coating vehicle;

(e) applying the coating vehicle to the surface of the medical device; and (f) drying the coated medical device.

In addition, the present invention provides an antimicrobial composition useful in applying an infection-resistant coating to medical devices which, in use, will exhibit a sustained activity rate over an appreciable time period.

DETAILED DESCRIPTION OF THE INVENTION

Surfaces which may embody the present invention can be generally any surfaces that contact patients or are important in health care, including table tops, hospital beds and various specific medical devices. Medical devices are those for use both externally and internally and include, for example, urinary, both internal and external, and intravenous catheters, contraceptives such as condoms, medical gloves, such as surgical and examination gloves, wound dressings, drainage tubes, orthopedic, penile and other implants, wound clips, sutures, hernia patches and arterial grafts. The devices or surfaces, sometimes generally together referred to as "surfaces" herein, can be made of a variety of natural or synthetic materials such as metals, plastics and polymers, and including Dacron®, rubber, latex, collagenous substances, silicone, polyurethane, polyvinyl chloride, Teflon®, polypropylene, polyethylene, poly(lactic acid), polyglycolic acid, cotton, silk, stainless steel, porous ceramics, and porcelain.

DEFINITIONS

The following specification refers to a number of microorganisms in describing the invention or its use. Unless otherwise stated, the following are the generally recognized names of the microorganisms, together with their source:

| Organism | Source |
| --- | --- |
| Stalphylococcus aureus | clinical isolate - Columbia Presbyterian Hosptial New York, New York |
| Staphylococcus epidermidis | clinical isolate - Columbia Presbyterian Hospital New York, New York |
| Esherichia coli | clinical isolate - Columbia Presbyterian Hospital New York, New York |
| Candida albicans | ATCC No. 11651 |

It is also noted that unless otherwise stated, the concentrations and ranges expressed as percentages (%), indicates the respective value based on weight of solid per volume of solvent. As an example, a 1% polyurethane in a solvent coating vehicle comprising tetrahydrofuran (THF) represents 1 gram of polyurethane in 100 ml of THF. On the other hand, in expressing relative proportions of two or more solvents in a coating vehicle, the percentages given are on a vol/vol basis.

Polymeric Coating Agent

The polymeric coating agent component of the coating vehicle of the present invention is selected from the group consisting of biomedical polyurethanes, biomedical silicones, biodegradable polymers and combinations thereof. It has been found that these particular polymeric materials enable the antimicrobial agent of the second embodiment of the invention to be retained and released in an active state on the coated medical device over an appreciable period of time, e.g., from about 12 to in excess of 21 days.

Selection of the coating vehicle depends upon the specific composition of the surface of the device to be coated, and the characteristics sought. For example, a polyurethane catheter is preferably coated with a formulation based on a biomedical polyurethane matrix-forming material. A silicone rubber catheter, on the other hand, preferably is provided with a coating having a silicone rubber as a matrix-forming material. It has also been discovered that a final thin coat of a silicone fluid after a first coating of biomedical polyurethane or of silicone rubber imparts surface glossiness and lubricity to the catheter. Thus, multiple, combined coatings, described in greater detail below, can also be achieved with improved characteristics.

In addition to polymeric coating compositions, the antimicrobial compositions of this invention may be applied to surfaces of medical devices in powder form, preferably under conditions which cause adherence of the powder to the surface of the device. For example, medical gloves, such as surgical or examination gloves fabricated from latex, polyurethane or polyvinyl acetate, may be coated with a powder containing the antimicrobial composition, as will be explained below in more detail.

A. Biomedical Polyurethane

In accordance with the first embodiment of the invention, the essential polymeric coating agent component of the coating vehicle is biomedical polyurethane, since it has been found unexpectedly that polymeric materials of this class enable the antimicrobial agent to be retained in an active state on the coated medical device and released over an appreciable period of time, e.g., from about 12 to in excess of 21 days, without altering the biocompatibility, lubricity and non-thrombogenicity of the surface. Suitable biomedical polyurethanes include both the ether-based polyurethanes and the ester-based polyurethanes described on pages 175–177 of *Controlled Release of Biologically Active Agents*, by Richard W. Baker, John Wiley and Sons, 1987; the ether-based compounds are preferred. A thorough discussion of a number of proprietary biomedical polyurethanes is found in *Polyurethanes in Medicine*, by Michael D. Lelah and Stuart L. Cooper, CRC Press, Inc., Fla 1986, pp. 57–67.

The following is a listing of proprietary biomedical polyurethanes that are useful in accordance with the invention:

1. Biomer®, which consists of 4,4-diphenylmethane-diisocyanate (MDI) and low molecular weight polytetramethyleneoxide (PTMO) segments with diamines as chain extenders. A proposed repeat unit chemical structure for Solution Grade Biomer® is:

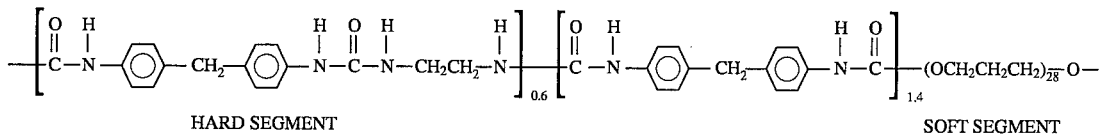

HARD SEGMENT · SOFT SEGMENT

2. Acuthane® is a block copolymer which contains 10% polymethylsiloxane and 90% polyetherurethane.

3. Pellethane® is an aromatic ether polyurethane. Pelletbane® 2363 (80AE) is not crosslinked and is readily soluble in dimethylacetamide, tetrahydrofuran, or N-ethyl pyrrolidone. The 90A of the same series contains crosslinks due to the excess of isocyanates present during the polymerization process and is therefore more difficult to solubilize.

4. Rimplast® is a silicone urethane made with either aliphatic or aromatic ethers or esters of polyurethane and a reactive, high molecular weight silicone to form an interpenetrating network (IPN).

We have found that best results are obtained using Pellethane® 2363-80AE, one of a series of thermoplastic, segmented elastomers sold under the designation Pellethane® by Dow Chemical Co. These materials are described at p. 60 of Lelah et al, Supra. Another suitable product is Biomer®, which is conveniently available as a 30 wt. % solution in N, N-dimethylacetamide (DMAC) described at pp. 57–58 of Lelah et al, supra. Another suitable material is Rimplast®, a series of biomedical urethanes containing silicones, reacted to form a series of interpenetrating network modified silicones containing polyurethanes. A description of these materials are found on pp. 61–63 of Lelah et al, supra.

The prior art, such as U.S. Pat. No. 4,667,143, fails to distinguish between various polymeric coating agents. The patent states that any one of a long list of resins may be mixed with an antimicrobial metal compound to provide antimicrobial coatings on medical devices. The working examples of the patent utilize either ABS polymers or alkoxy curing RTV silicone rubbers. Quite unexpectedly we have found that the specific application of biomedical polyurethanes as a coating agent is superior to all other known polymeric coating materials. This discovery was made by first determining the relative solubilities of various polymeric coating agents in equal amounts of DMAC and ethylacetate. The results of this screening test are shown in Table I.

TABLE I

Solubility of Various Polymers in Solvent Comprising 50% DMAC + 50% Ethyl Acetate

| | |
|---|---|
| 1. POLY (ETHYLENE) | NS |
| 2. POLY (METHYL METHACRYLATE) | S |
| 3. POLY (ETHYLENE-MALEIC ANHYDRIDE) | NS |
| 4. POLY (CAPROLACTONE) | S |
| 5. POLY (VINYL ALCOHOL) MW 25,000 | NS |
| 6. POLY-3-HYDROXYBUTYRATE $5 \times 10^5$ | NS |
| 7. POLY (ETHYLENE OXIDE) MW 4,000,000 | NS |
| 8. POLY (BUTANEDIOL-1, 4-TERE-PHTHALATE) | NS |
| 9. POLY (HEXAMETHYLENE DODECANEDIAMIDE) NYLON | NS |
| 10. POLY (VINYL ACETATE) MW 500,000 | S |
| 11. POLY (VILIDENE CHLORIDE-ACRYLONITRILE) 80:20 | S |
| 12. POLY (HEXAMETHYLENE SEBACAMIDE) NYLON | NS |
| 13. POLY (PROPYLENE, ISOTACTIC) | NS |
| 14. POLY (ETHYL METHACRYLATE) | S |
| 15. POLY (STYRENE-MALEIC ANHYDRIDE) | S |
| 16. POLY (STYRENE ALLYL ALCOHOL) | S |
| 17. POLYACRYLAMIDE | NS |
| 18. POLY (ISO-BUTYL METHACRYLATE) | S |
| 19. POLY (VINYL PYRROLIDONE) | S |

TABLE I-continued

Solubility of Various Polymers in Solvent Comprising 50% DMAC + 50% Ethyl Acetate

| | |
|---|---|
| 20. POLY (PROPYLENE, CHLORINATED, 65%) | S |
| 21. POLY (N-BUTYL METHACRYLATE-ISOBUTYL METHACRYLATE 50/50) | S |
| 22. POLY (VINYL CHLORIDE-VINYL ACETATE) | S |
| 23. POLY (ACRYLIC ACID) MW 4,000,000 | NS |
| 24. POLY (HEXAMETHYLENE ADIPAMIDE) | NS |
| 25. POLY (N-BUTYL METHACRYLATE) | S |
| 26. POLY (CARBONATE BISPHENOL A) | NS |
| 27. POLY (LAURYL LACTIM) | NS |
| 28. POLY (CAPROLACTAM) | NS |
| 29. POLY (ACRYLAMIDE-ACRYLIC ACID SODIUM SALT) 70% CARBOXYL HIGH CARBOXYL MW 200,000 | NS |
| 30. POLY (VINYL ALCOHOL) 88% MOLE HYDROLYZED, MW 25,000 | NS |
| 31. POLY (ACETAL) RESIN | NS |
| 32. POLY (STYRENE-ACRYLONITRILE 75:25) | S |
| 33. POLY (METHYL VINYL ETHER/MALEIC ANHYDRIDE) | NS |
| 34. POLY (SULFONE) RESIN | S |
| 35. POLY (VINYLDIENE FLUORIDE) | S |
| 36. POLY (TETRAFLUOROETHYLENE) | NS |
| 37. POLY (VINYLDIENE CHLORIDE/VINYL CHLORIDE 86:12) | S |
| 38. POLY (VINYL BUTYRAL) MW 100,000–150,000 | S |
| 39. POLY (p-VINYL PHENOL) | S |
| 40. POLY (ETHYLENE-ACRYLIC ACID 92:8) | NS |
| 41. POLYURETHANE (DOW PELLETHANE ® 2363-80AE) | S |

S = READILY SOLUBLE
NS — NOT SOLUBLE

After rejecting the insoluble polymers, steps were taken to coat the soluble polymers, i.e., those identified in Table I as numbers 2, 4, 10, 11, 14, 15, 16, 18, 19, 20, 21, 22, 25, 32, 34, 35, 37, 38, 39, and 41, upon catheters to determine which formed stable, workable coatings. Both urinary and I.V. catheters were used, and for this test, the urinary catheter was fabricated of latex and the I.V. catheter of Pellethane® 2363, 90A, described above.

Two different coating formulations were used having the following formulations:

1. 1% chlorhexidine acetate (CHA)+6% polymer in a solvent consisting of 50% DMAC+50% ethyl acetate (EA)
2. 2% CHA+6% polymer in a solvent consisting of 50% DMAC+50% EA The key characteristics of glossiness, smoothness, and stickiness of the exposed coating surface as well as the degree of adhesion of the coating to the catheters' surfaces of the coated polymers were then compared, and the results are shown in Table II.

TABLE II

Quality of Coating on the Polyurethane Catheter (I.V.) and the Latex (URO) Urinary Catheter

| | IV GLOSSINESS | URO GLOSSINESS | IV SMOOTHNESS | URO SMOOTHNESS | IV STICKINESS | URO STICKINESS | IV ADHESION | URO ADHESION |
|---|---|---|---|---|---|---|---|---|
| 2 | YES | YES | YES | YES | SLIGHT | YES | GOOD | POOR |
| 4 | SEMI | SEMI | YES | YES | NO | NO | GOOD | GOOD |
| 10 | YES | YES | YES | YES | NO | NO | GOOD | POOR |
| 11 | SEMI | SEMI | NO | NO | NO | NO | GOOD | POOR |
| 14 | SEMI | SEMI | YES | YES | SLIGHT | NO | GOOD | POOR |
| 15 | YES | YES | YES | YES | NO | NO | GOOD | GOOD |

TABLE II-continued

Quality of Coating on the Polyurethane Catheter (I.V.) and the Latex (URO) Urinary Catheter

| | IV GLOSSINESS | URO GLOSSINESS | IV SMOOTHNESS | URO SMOOTHNESS | IV STICKINESS | URO STICKINESS | IV ADHESION | URO ADHESION |
|---|---|---|---|---|---|---|---|---|
| 16 | YES | YES | YES | YES | NO | NO | GOOD | GOOD |
| 18 | NO | NO | YES | YES | NO | NO | GOOD | GOOD |
| 19 | YES | YES | YES | YES | YES | YES | GOOD | GOOD |
| 20 | SEMI | NO | YES | YES | SLIGHT | NO | GOOD | GOOD |
| 21 | NO | NO | YES | YES | SLIGHT | NO | GOOD | GOOD |
| 22 | YES | YES | YES | YES | YES | NO | GOOD | POOR |
| 25 | NO | NO | YES | YES | YES | NO | GOOD | GOOD |
| 32 | YES | YES | YES | YES | YES | NO | GOOD | POOR |
| 34 | NO | NO | MEDIUM | YES | NO | SLIGHT | GOOD | POOR |
| 35 | NO | NO | YES | YES | YES | YES | GOOD | POOR |
| 37 | SEMI | NO | YES | MEDIUM SMOOTH | YES | YES | GOOD | FAIR |
| 38 | NO | SEMI | NO | YES | YES | YES | GOOD | POOR |
| 39 | YES | SEMI | YES | YES | SLIGHT | NO | GOOD | GOOD |
| 41 | YES | YES | YES | YES | NO | NO | GOOD | GOOD |

Coating Formulas:

URO = 6% Polymer + 1% CHA in $\frac{50}{50}\frac{DMAC}{EA}$

I.V. = 6% Polymer + 2% CHA in $\frac{50}{50}\frac{DMAC}{EA}$

Thus, although several polymers can be used as controlled delivery matrices, biomedical polyurethane, number in Table II, was found to possess across-the-board superior characteristics.

Glossiness, smoothness, and stickiness of the exposed coating surface as well as adhesion of the coating to the device are crucial characteristics. Equally important to the invention is the coating agent's ability to absorb and release, in a controlled-dosing manner, bio-active agents. Again, biomedical polyurethane was far superior, and the results are shown in Table III, below. For this comparison, chlorhexidine diacetate (CHA) was incorporated into solutions of each of the polymers found to be soluble as listed in Table I.

TABLE III

Comparative Matrices Days of Activity

| POLYMER MATRIX SYSTEM | I.V. | URO |
|---|---|---|
| 1. POLY (METHYL METHACRYLATE) | 3 | NT |
| 2. POLY (CAPROLACTONE) | 3 | NT |
| 3. POLY (VINYL ACETATE) MW = 500,000 | 2 | NT |
| 4. POLY (VINYLDIENE CHLORIDE-ACRYLONITRILE) 80:20 | 1 | NT |
| 5. POLY (ETHYL METHACRYLATE) | 2 | NT |
| 6. POLY (STYRENE-MALEIC ANHYDRIDE) | 0 | 0 |
| 7. POLY (STYRENE-ALLYL ALCOHOL) | 1 | 1 |
| 8. POLY (ISO-BUTYL METHACRYLATE) | 2 | 2 |
| 9. POLY (VINYL PYRROLIDONE) | 2 | 2 |
| 10. POLY (PROPYLENE, CHLORINATED) 65% | 2 | 2 |
| 11. POLY (N-BUTYL METHACRYLATE-ISO-BUTYL METHACRYLATE) 50/50 | 2 | 2 |
| 12. POLY (VINYL CHLORIDE-VINYL ACETATE) | 2 | NT |
| 13. POLY (N-BUTYL METHACRYLATE) | 1 | 2 |
| 14. POLY (STYRENE-ACRYLONITRILE) 75:25 | 2 | NT |
| 15. POLY (SULFONE) RESIN | 1 | NT |
| 16. POLY (VINYLDIENE FLUORIDE) | 1 | NT |
| 17. POLY (VINYLDIENE CHLORIDE/VINYL CHLORIDE) 88:12 | 1 | 2 |
| 18. POLY (VINYL BUTYRAL) MW = 100,000–150,000 | 3 | NT |
| 19. POLY (p-VINYL PHENOL) | 1 | 0 |
| 20. POLY (URETHANE) DOW PELLETHANE ® | >4 | >4 |
| 21. PTUE 205 RIMPLAST ® | 3 | 3 |

I.V. = intravenous catheter fabricated of Pellethane ® 2363, 90A
URO = urinary catheter fabricated of latex
NT = not tested due to poor film formation or lack of adhesion of coating to substrate.

The coating formulas used in preparing coating vehicles for Table III were:
1. Urinary Catheters: 1% CHA+6% Polymer in solvent.
2. I.V. Catheters: 2% CHA+6% Polymer in solvent.

In both cases, the solvent consisted of 50% dimethylacetamide and 50% ethyl acetate.

The results given in Table III were obtained using the following bioassay:
1. Latex Urinary Catheters: 2 cm. sections were soaked in 5 cc of Trypticase Soy Broth (TSB) and challenged with $10^4$ CFU of a 1:1 mixture of *Staph. epidermidis* and *E. coli* pre-diluted to 0.3 optical density at 600 nm.
2. Polyurethane I.V. Catheters: 2 cm. sections thereof were soaked as above and challenged with $10^4$ CFU of *Staph. aureus*, again pre-diluted to 0.3 optical density at 600 nm. This was a severe test, where the catheters were challenged daily with a broth culture having $10^4$ CFU of the bacteria. The results show superior performance of biomedical polyurethane in maintaining sustained activity for more than four days for both types of catheters when coated with Pellethane® 2363 (line 21) and three days for Rimplast® PTUE 205, a silicone IPN modified urethane. The other resins averaged only one to two days.

The superior characteristics of the biomedical polyurethanes, lines 20 and 21, are surprising, since the prior art does not hint or suggest that any one of the above polymer matrices is any better than any other. Instead, the art teaches a general and uniform performance from each.

As a consequence of these results, several factors are postulated to account for the superior performance of biomedical polyurethane.

Polymer Backbone Rotational Flexibility:

It is well established that apart from the molecular weight of a solute, solubility in a polymer depends on the ability of the backbone of that polymer to rotate about one or more axes. Polyurethane's backbone flexibility falls somewhere in between the extreme freedom of rotation found in the silicone rubbers to the inflexibility of polystyrene. Since polyurethane is a segmented block copolymer made of both hard and soft segments it combines the ability of readily releasing bio-active agents from the amorphous phase with the slow release, reservoir-like characteristics of the hard or crystalline domain. Intramatrix diffusion probably occurs as the bio-active drug levels in the soft domains drop, causing a gradient related flow of solute out of the crystalline phase into the more flexible areas which then in turn diffuses out into the environment.

Progressive Formation of Interconnected Diffusion Channels:

As the drug molecules at the surface of the matrix are dissolved, the solute (blood, perspiration, saline, media etc.) is allowed to penetrate into the film, thus forming microchannels which further facilitate the release process. The pore formation is likely proportional to the flexibility of the backbone of the polymer, whereby the rate of channeling falls as the domain becomes more crystalline.

Polyurethane has, on the average, 75 to 100 times the water absorption of silicone (RTV) and 25 times that of polystyrene. The greater value for polyurethane is probably due to the hydrophilic nature of the soft segment and presumably means that channel formation is enhanced.

Electrical Properties of the Matrix:

The charge that a polymer carries influence the affinity of the antimicrobial agent for the matrix. In some cases, such as when the antimicrobial agents silver (Ag) or chlorhexidine acetate (CHA) are mixed with latex, the binding is so strong that ions of the antimicrobial agent are restricted in their ability to diffuse out of the matrix. Some biomedical polyurethanes carry a positive charge and therefore do not react with, and thus inactivate, cationic antimicrobial agents such as Ag or CHA. Anionic compounds such as piperacillin or sulfadiazine are relatively unreactive and extremely soluble so that they do not bind to polyurethane and are released at a steady and prolonged rate.

Thus, the polymeric coating agent component cannot be polyethylene vinyl acetate, polyvinyl chloride or polyvinyl alcohol, because such polymers give unsatisfactory results. As mentioned above, the polymer of choice is a polyether polyurethane and, more specifically, Pellathane® 2363-80AE. It has been further found that this polymer in solvent must critically range from 1–10%, and preferably 2–6%, and most preferably 3% by volume, for best performance.

B. Biomedical Silicones

Suitable biomedical silicones include the silicone rubbers or elastomers described on pp. 156–162 of *Controlled Release of Biologically Active Agents*, by Richard W. Baker, John Wiley and Sons, 1987.

Silicone rubbers having the general formula

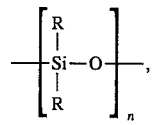

where R is either a methyl or a —$C_6H_6$ substituent, are useful. More specifically, the following proprietary biomedical silicones may be used:

1. Silastic® Type A Medical Adhesive, a polydimethyl siloxane sold by Dow Corning and which is a one component system which cures at ambient room temperature and humidity. Its formula is:

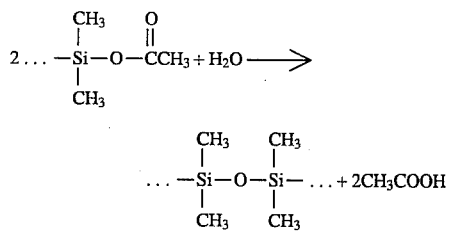

2. Other Silastic® products that can be used to form time release matrices include:
   (a) Q72213—a medical grade dispersion of silicone in trichloroethane;
   (b) Silastic® 360; and
   (c) MDX4-4159, a proprietary product of Dow Corning containing 50% of an amino functional polydimethyl siloxane copolymer and 50% of mixed aliphatic and isopropanol solvents.
3. Two component vinyl curing silicone—a dimethyl silicone compound with a vinyl terminated prepolymer component is reacted to the backbone of a second silicone component.

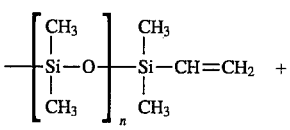

Vinyl-terminated
silicone plus catalyst
(prepolymer)

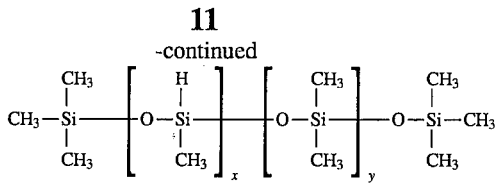

Methyl hydrogen silicone
(curing compound)

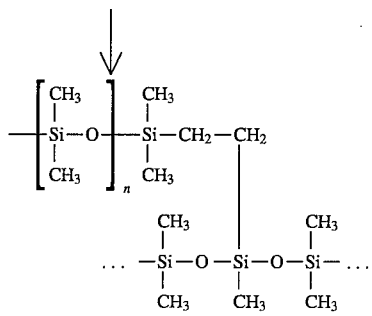

4. Two component curing silicone—Silastic® 382 is an example of a silicone which cures by condensation whereby a prepolymer containing a hydroxy group is crosslinked by the addition of a methoxysilane and catalyst.

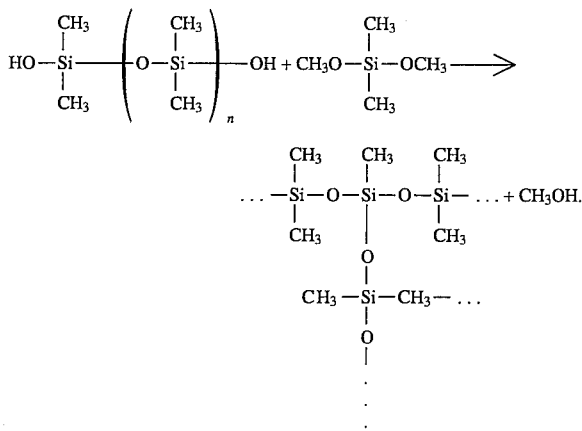

It is preferred to employ room temperature curing materials. It is also preferred to employ a mixture of equal parts of a polydimethyl siloxane such as Silastic® Type A adhesive and a mixed amino functional polydimethyl siloxane copolymer such MDX4-4159 in mixed aliphatic and isopropanol solvents, to provide a coating surface having a smooth surface and extended period of activity.

The selection of specific polymeric coating agent to form a coating matrix will depend upon the nature of the surface to which the coating will be applied. It is preferred that a biomedical polyurethane be applied to a polyurethane surface to assure good coating adherence. A biomedical silicone, such as a mixture of Silastic® Type A Medical Adhesive and MDX4-4159, is suitable to coat a device that is fabricated of silicone, polyurethane or of latex.

C. Biodegradable Polymers

It has further been found that use of a biodegradable polymer in the coating composition of this invention, either alone or in combination with one or more of the other biomedical polymers, enhances the character of the polymer matrix. Suitable biodegradable polymers include the homopolymers poly(glycolic acid), poly(D-lactic acid), poly(D,L-lactic acid), poly(D,L-ethylglycolic acid), poly(dimethylglycolic acid), poly(D, L-methylethylglycolic acid), and poly(E-caprolactone), as well as biodegradable polyhydroxy butyric acid and mixtures thereof. A preferred biodegradable polymer is polylactic acid (PLA).

Thus biodegradable polymer may be added to biomedical polyurethane in the quantities indicated herein. The biodegradable polymer modulates the rate of release of antimicrobial drugs. The initial burst of drug which occurs during the first few days after implantation is more or less eliminated since the drug is bound in the biodegradable polymer and will be released only when degradation of the polymer occurs. Inclusion of a biodegradable polymer such as PLA in the matrix gives prolonged biocidal activity as confirmed in in vitro studies, shown in Table IV, below.

TABLE IV

Enhanced Efficacy of Polyurethane + PLA Matrix

| Coating Composition | Days of Activity* |
|---|---|
| 1. 3% DPU + 3% CHA | 4 |
| 2. 3% DPU + 1% PLA + 3% CHA | 6 |
| 3. 3% DPU + 1% AgSD + 1% CHA | 4 |
| 4. 3% DPU + 1% PLA + 1% AgSD + 1% CHA | 5 |

DPU = Pellethane ® 2363-80AE - Dow Chemical Co.
PLA = poly (lactic acid) molecular weight of 100000
AgSD = silver sulfadiazine
CHA = chlorhexidine diacetate
Solvent = 25 parts of ethanol and 75 parts of tetrahydrofuran (THF)
*determined according to the bioassay set forth above with regard to Table III An additional advantage of using a biodegradable polymer such as PLA in a polyurethane matrix is to allow improved tissue ingrowth simultaneously with a prolonged antimicrobial effect as the biodegradable polymer degrades. Thus, this embodiment of the invention is particularly important in orthopedic applications as well as in such devices as arterial grafts where there is a need for formation of the pseudo-intima or the growth of tissue into the interstices of orthopedic implants and arterial grafts, as well as cuffs which anchor IV catheters in place.

Suitable biomedical poly(lactic) polymers include the poly(L-lactide), poly (D-lactide) and the poly(D-L-lactic acid). These materials are described, inter alia, on pp. 87, 88 and 115, of Baker, s. Upra, and are biodegradable. Poly(L-lactic) acid is preferred, and those polymers having a range of molecular weights ranging from 2000 to 300,000 have been used with success.

Poly(D, L-lactic acid)

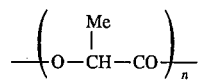

Poly(D-lactic acid)

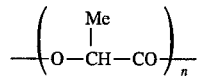

The poly(lactic acid) polymers are bioerodable, and while they can be used alone, it is preferred that they be combined with either a biomedical polyurethane or a biomedical silicone.

As in the first embodiment of the invention, an additional advantage of using PLA in a polyurethane matrix is to allow improved tissue ingrowth simultaneously with a prolonged antimicrobial effect as the PLA degrades. Thus, this embodiment of the invention is particularly important in orthopedic applications as well as in such devices as hernia patches and arterial grafts where there is a need for formation of the pseudo-intima or the growth of tissue into the interstices of orthopedic implants and arterial grafts, as well as cuffs which anchor I.V. catheters in place.

Solvents

The solvents used in preparing the coating vehicle used in the present invention includes solvents for the biomedical polymeric coating agent and/or the antimicrobial agent, and include acetic acid, methyl acetate, ethyl acetate, hexane, N-N-dimethylacetamide (DMAC), tetrahydrofuran (THF), alcohols (e.g., alkanols), water, N-ethyl-2-pyrrolidone (NEP), n-(2-hydroxy-ethyl)-2-pyrrolidone, n-cyclohexyl-2-pyrrolidone and combinations thereof. The selection of a particular solvent or mixture of solvents will depend upon the specific biomedical polymeric coating agent being used as well as upon the particular antimicrobial agent or combination of agents.

Certain desired solvents for the polymeric coating agent may not be good solvents for an antimicrobial agent of choice. In that case, a solvent is selected which will dissolve the antimicrobial agent and will be miscible with the solvent solution of polymeric coating agent. Thus, a solvent solution of the antimicrobial agent may be combined with the biomedical polyurethane in solution in its solvent and the two solutions thereafter combined to form a uniform mixture.

Another important consideration in selecting a solvent is that the resulting solution will readily adhere to and form a film on the surface to which it is applied. Certain solvent solutions containing certain polymers do not adequately wet latex surfaces, for example, with the result that the coating is discontinuous or non-adherent.

In a preferred coating mixture where it is desired to incorporate chlorhexidine acetate with a biomedical polyurethane as coating agent, a preferred solvent is the combination of ethanol and THF, preferably in the proportions of 10% ethanol and 90% THF. Good results have been obtained where this combination contains from 1 to 25% ethanol. Another preferred combination for use with chlorhexidine acetate is NEP and THF, over a range of 1.0 to 10% NEP, more preferably 5%. Still further useful combinations of solvents include DMAC and ethyl acetate, containing from 1 to 50% DMAC, and DMAC and THF, with 1 to 25% DMAC. Each of these preferred solvent combinations results in a coating vehicle which readily wets and adheres to surfaces of medical devices fabricated from medical polyurethane, latex and/or silicone polymer, but also provides a superior adherent coating.

Antimicrobial Agents

Antimicrobial agents useful according to this first embodiment of the invention include the biguanides, especially chlorhexidine and its salts, including chlorhexidine acetate, chlorhexidine gluconate, chlorhexidine hydrochloride, and chlorhexidine sulfate, silver and its salts, including silver acetate, silver benzoate, silver carbonate, silver iodate, silver iodide, silver lactate, silver laurate, silver nitrate, silver oxide, silver palmitate, silver protein, and silver sulfadiazine, polymyxin, tetracycline, aminoglycosides, such as tobramycin and gentamicin, rifampicin, bacitracin, neomycin, chloramphenicol, miconazole, quinolones such as oxolinic acid, norfloxacin, nalidixic acid, pefloxacin, enoxacin and ciprofloxacin, penicillins such as oxacillin and pipracil, nonoxynol 9, fusidic acid, cephalosporins, and combinations thereof.

From the above list, unexpectedly, some special combinations have been found. The combination of the biguanides, especially chlorhexidine and its salts with silver salts cause a special synergistic sustaining of antimicrobial action, as described in the second embodiment of the invention below. The biguanides are also synergistically effective with nalidixic acid and its derivatives. Another effective combination is chlorhexidine acetate and pipracil.

Where the antimicrobial agent used is insoluble in the coating vehicle, as is the case with most of the silver salts and the water insoluble chlorhexidine, it is preferred that the agent be very finely subdivided, as by grinding with a mortar and pestle. A preferred product is micronized, e.g., a product wherein all particles are of a size of 5µ or less. In the case of the preferred silver sulfadiazine, a micronized product may be used.

The antimicrobial agent is preferably employed in the coating vehicle at a level such that the final coating contains from 10 to 70% by weight of the antimicrobial agent. This may be accomplished by providing a concentration of, for example, 0.5 to 3%, preferably 1%, of chlorhexidine acetate and 0.5 to 5%, preferably 1%, of silver sulfadiazine in the coating vehicle.

Unique to the invention is the use of chlorhexidine since such use internally, that is, in the human body, is heretofore unknown. Though there are examples available on the use of chlorhexidine in the bladder, such data is not relevant hereto, since it is not truly an internal use as there is no contact with the patient's circulation.

The absence of even a hint of using chlorhexidine internally is due, at least in part, to its relatively high toxicity and chemical nature (highly polar, reactive, high affinity for lipids and proteinaceous materials), leaving it a poor candidate as a systemic drug. The only way to use chlorhexidine internally is in the time release matrix system described above that allows for a dose that is non-toxic to the patient but effective against microorganisms.

Coating Vehicle

The coating vehicle is prepared according to the invention by dissolving the polymeric coating agent in a solvent therefor and by combining this solution with a solution or suspension of the antimicrobial agent. These materials can be combined at room temperature or at a slightly elevated temperature with the aid of agitation. It is preferred to employ solvents with readily evaporate from the coating at room temperature, or at an elevated temperature below that which inactivates the antimicrobial agent.

In the case of a preferred antimicrobial composition chlorhexidine acetate, either alone or in combination with silver sulfadiazine, the coating vehicle is prepared by first dissolving the polymeric coating agent such as the biomedical polyurethane in a solvent therefor, such as tetrahydrofuran (THF). The chlorhexidine is then dissolved in a solvent therefor, such as ethanol, water, or preferably N-ethyl-2-pyrrolidone (NEP), which is also miscible with THF.

Other Agents in Coating Matrix

In addition to antimicrobial agents and matrix forming materials, the coatings of the present invention may contain other compatible ingredients to advantage. For example, where anti-blood clotting activity is desired, heparin may be used, preferably at a level of 0.2%. Another useful ingredient is dextran sulfate, preferably also at a level of 0.2%

In accordance with the method of this invention, the medical device can be coated with the coating composition by known coating techniques, such as dip coating, spray coating, brush coating, roller coating, etc. Moreover, multiple coatings using the same or different polymer matrix-forming agents for each, can be used.

The coated medical device can be dried at room temperature to remove solvent or with the aid of a slightly elevated temperature over an appropriate time period.

The coating method can be repeated to build up a thicker coating on the medical device and/or to use a different antimicrobial agent in each coating, if desired.

In accordance with another preferred embodiment of the invention, the antimicrobial composition of this invention comprising a mixture of a biguanide and a silver salt in powder form is applied directly to the surface of a medical device. The method of application is one which assures adherence of the powder to the surface. One such method applies the powdered antimicrobial agent to an adhesive surface in micro layers so that minimum loss of adhesiveness occurs while imparting a high level of protection against growth of microorganisms to the surface. Other procedures include mixing the powder with adhesive prior to its application, and providing areas on the surface which alternatively contain adhesive and powdered antimicrobial agent. In one preferred method, a powder comprising a mixture of biguanide and a silver salt, most preferably a mixture of silver sulfadiazine and chlorhexidine acetate, was applied to rubber gloves at a point during their manufacture when the rubber was soft and/or semi-molten. The powder was found to adhere well after cooling of the gloves to room temperature.

It will further be understood that the invention does not require coating both the inside and outside of medical devices, especially catheters. In fact, it has been found that some catheters coated only on the outside provide necessary prophylaxis, without chemical or biological interference with the materials added to the body by the catheter. There may be instances when, for example, a coating containing an antimicrobial agent and heparin is applied only on the outside of an I.V. catheter used for providing blood to a patient. In other instances, it is advantageous to apply a coating with the anti-coagulent on the inside of the catheter to prevent clotting blockages. These specific selections are all within the scope of the invention.

Concentrations of the coating vehicle, the antimicrobial composition, the coating composition and resultant coating can be selected as desired and as illustrated by the following representative examples. In the case of the preferred combination of chlorhexidine acetate and silver sulfadiazine, good results have been obtained when the agents are present in a proportion ranging from 1:9 to 9:1, respectively. Further, it is preferred that this combination of antimicrobial agents be present at levels of from 10 to 70% by weight of the final coating.

The invention will be further illustrated by the following examples. Unless indicated otherwise, the silver sulfadiazine (AgSD) used in the examples was a micronized powder product having a particle size of 5μ or less.

It is recognized, however, that silver or its salts, including silver sulfadiazine, having a larger average particle size are useful according to this invention, and particle size selection will depend on the contemplated use of the medical device.

EXAMPLE 1

A coating vehicle for use in accordance with the present invention was prepared as follows:

1 gm of chlorhexidine acetate (CHA) was added to 5 cc of N-ethyl-2-pyrrolidone (NEP). The mixture was heated to 50°–60° C. and agitated in a Vortex® stirrer until the CHA dissolved.

10 cc tetrahydrofuran (THF) was then added to the CHA solution in NEP and the mixture thoroughly agitated to form a uniform solution.

3 gm of Pellethane® 2363-80AE of the Dow Chemical Co. was added to 50 cc of THF. The mixture was warmed to about the boiling point of THF, 65°–70° C., and stirring with a Vortex® stirrer was continued until the polyurethane was dissolved.

1 gm of silver sulfadiazine (AgSD) powder was suspended in 35 cc of THF and vigorously agitated in a Vortex® stirrer to form a uniform suspension. The CHA solution in NEP and THF prepared above was then combined with the polyurethane solution and agitated to form a clear solution. As a last step in preparing the coating vehicle, the AgSD suspension in THF was added and the entire mixture agitated to maintain a uniform suspension. Thus was provided a coating vehicle containing 1% CHA and 1% AgSD as antimicrobial agents, together with 3% of the biomedical polyurethane. The solvent in this case was a mixture of solvents comprising 5% NEP and 95% THF. The CHA was in solution in the coating vehicle, while the AgSD was in uniform suspension.

The coating vehicle prepared above was used to coat an I.V. catheter fabricated of Pellethane® 2363-90A. The catheter was dipped in the coating vehicle while the vehicle was being continuously agitated to insure a uniform suspension. The coated catheter was then dried. A tightly adherent coating on the catheter was thus provided. A bioassay of sections of the catheter performed in accordance with the test given above with respect to Table III showed sustained activity against the microorganisms for in excess of eight days.

EXAMPLE 2

Methods of Preparing I.V. and Urinary

Catheters Coated with Soluble Silver

Salts and Water Insoluble Chlorhexidine

In certain instances, it is necessary to use antimicrobial agents starting in solution rather than as comminuted solids. Though the invention comprises both, coating with the precursors of certain antimicrobial agents in solution has been found to be best achieved in one of two ways:

Method 1

Coating vehicle contains 1% AgNO$_3$+1–3% water insoluble free-base chlorhexidine+6% polyurethane in DMAC/ethyl acetate mixture (1:1).

Water insoluble chlorhexidine is first prepared by precipitating the chlorhexidine from chlorhexidine acetate. This chlorhexidine is used for coating purposes in those instances where the chlorhexidine salts are reactive with other ingredients of the coating vehicle. For example, the acetate or gluconate salts of chlorhexidine react with silver nitrate instantly in aqueous solutions with the undesired result that each is inactivated.

Preparation of 100 ml coating vehicle. 1 gm silver nitrate and 1 gm water-insoluble free-base chlorhexidine were dissolved separately in 10 ml portions of DMAC. 6 gm polyurethane, Pellethane® 2363-80AE, were dissolved in 30 ml DMAC and mixed with the silver nitrate and chlorhexidine solutions. 50 ml ethyl acetate was mixed with this solution to form a coating vehicle and used for coating.

Method 2

Coating vehicle contains 0.3% AgNO$_3$+0.75% sulfadiazine+1–2% chlorhexidine+6% polyurethane in DMAC/ethyl acetate mixture (1:1).

The method of preparation of this coating solution is the same as described in Method 1 except that the sulfadiazine is added to the chlorhexidine solution and a uniform dispersion formed. The medical device (e.g., catheter) is dipped, sprayed or painted, at least once, with this solution.

A series of catheters were coated with the coating solutions prepared by methods 1 and 2 in this example and compared with a commercially available catheter coated with silver oxide. Catheters numbers 2 and 6 were prepared in accordance with method 1 above. Catheters numbers 3, 5 and 7 were prepared by method 2 above. Catheters numbers 1 and 4 were prepared in accordance with the method and using the formulation following Table I, the chlorhexidine in catheter 4 being the water insoluble type referred to in method 1 above.

The tests recorded in Table V are described elsewhere in this specification. The activity in trypticase soy broth (TSB) was determined by the bioassay described as follows:
1. Latex Urinary Catheters: 2 cm sections were soaked in 5 cc of trypticase soy broth (TSB) and challenged with $10^4$ CFU of 1:1 mixture of *Staph. epi* and *E. coli* prediluted to 0.3 optical density at 600 nm.
2. Polyurethane I.V.: 2 cm sections soaked as above and challenged with $10^4$ CFU of *Staph. aureus*.

The zone of inhibition determination was made following Bioassay A, described in Example 5. The Agar Lumen test was conducted as follows:

5 cc of trypticase soy agar (TSA) was solidified in a culture tube. A cork borer was used to remove a central core of agar from the tube leaving a lumen into which a 4 cm section of a coated catheter having an outside dimension approximating that of the lumen opening was inserted. 1.2 cc of sterile urine was introduced into the lumen before the catheter was inserted. Once the catheter was inserted, an inoculum comprising a suspension containing $2 \times 10^5$ CFU of a mixture of 50% *Escherichia coli* and 50% *Staphylococcus epidermidis* was swabbed around the upper opening of the lumen adjacent the catheter.

The culture tube was incubated at 37° C. Once in each subsequent 24 hour period over the course of the test, 0.2 cc of urine was removed from within the catheter and lumen and the lumen was supplied with a fresh quantity, 0.2 cc, of sterile urine, which had just been inoculated with $2 \times 10^5$ CFU of the 50% *E. coli* and 50% *Staph. epi* inoculum. At the same time, 0.01 cc of the solution removed from the lumen was tested by subculturing on a blood agar plate to determine the presence or absence of microorganisms in the liquid. In Table V below is given the number of days before growth of microorganisms was observed, either visually in the agar surrounding the lumen or in the urine samples analyzed on blood agar plates.

Comparative results between commercially coated catheters and those coated in accordance with this invention further demonstrated the significant improvement obtained; the greater the zone of inhibition, the greater the degree of suppression and cidal tendencies. Table V, below gives the results of this series of tests.

TABLE V

Antibacterial Efficacy of Urinary Catheter

| Drugs in Catheter Coating | Agar Lumen Test (Days) | Zone of Inhibition (mm) | Activity in Presence of TSB (Days) |
| --- | --- | --- | --- |
| 1. Silver Sulfadiazine | 7 (static) | 11 | 2 |
| 2. Silver nitrate | 5 (static) | 9 | 1 |
| 3. Silver nitrate + sulfadiazine | 7 (static) | 11 | 2 |

TABLE V-continued

Antibacterial Efficacy of Urinary Catheter

| Drugs in Catheter Coating | Agar Lumen Test (Days) | Zone of Inhibition (mm) | Activity in Presence of TSB (Days) |
| --- | --- | --- | --- |
| 4. Chlorhexidine | >15 (cidal) | 20 | >10 |
| 5. Silver sulfadiazine + chlorhexidine | >15 (cidal) | 20 | >10 |
| 6. Silver nitrate + chlorhexidine | >15 (cidal) | 20 | >10 |
| 7. Silver nitrate + sulfadiazine + chlorhexidine | >15 (cidal) | 20 | >10 |
| 8. Silver oxide (Baxter Travenol) | 1 (static) | 10 | 0 |
| 9. No drug (Control) | 0 | 0 | 0 |

EXAMPLE 3

Multicoating

At times, urinary catheters or intravenous catheters coated with biomedical polyurethane and bio-active agents or silicone (with or without PLA) and bio-active agents are found to possess surface characteristics not fully desirable. To overcome this problem, the invention further comprises the provision of a second (or more) coatings.

It has been found that a second coating applied over the biomedical polyurethane coating by spraying, dipping or otherwise, of between 0.5 to 5% of a silicone such as MDX4-4195, Dow Corning, in solution in hexane, preferably 2%, after drying, renders the coated medical device, especially a catheter, smoother in texture, with improved lubricity, without interfering with the controlled release characteristics, as shown in Table VI.

TABLE VI

Retention of Antibacterial Efficacy in Presence of TSB Culture

| Drug Coated Catheter Sample | Bacterial Growth Days | | | | | | |
| --- | --- | --- | --- | --- | --- | --- | --- |
|  | 1 | 2 | 3 | 4 | 5 | 6 | 7 |
| 1 | 0 | 0 | 0 | 0 | 0 | 0 | 0 |
| 2 | 0 | 0 | 0 | 0 | 0 | 0 | 0 |
| 3 | 0 | 0 | 0 | 0 | 0 | 1+ | 2+ |
| 4 | 0 | 0 | 0 | 0 | 0 | 0 | 0 |
| 5 | 0 | 0 | 0 | 0 | 1+ | 2+ | 4+ |
| 6 | 0 | 0 | 0 | 0 | 0 | 0 | 1+ |
| 7 | 0 | 0 | 0 | 0 | 0 | 0 | 1+ |
| 8 | 0 | 0 | 0 | 0 | 0 | 0 | 1+ |
| 9 | 0 | 0 | 0 | 0 | 0 | 0 | 1+ |
| Control Catheter No Antimicrobial Agent | Heavy (+ +) | | | | | | |

2 cm segments of drug coated catheters (AgSD+CHA) in a biomedical polyurethane coating agent of 3% Pellethane® 2363-80AE in a solvent of THF+ethanol or DMAC+ethylacetate were coated with a second coating by applying thereto a 2% solution of MDX4-4195 in hexane. After thorough drying to remove solvent, the segments were suspended in 5 ml TSB containing $10^4$ *Staph. aureus* and incubated at 37° C. Every 24 hours, for seven days, the bacterial growth in the culture was measured by visual turbidity and colony counts and the catheter segment was transferred to fresh culture and the experiment repeated.

Bacterial growth was properly suppressed for seven days. In addition, the catheters possessed smoother surfaces. This multi-coating process can also use PLA in the first coating, and over a range of 0.2 to 2%, preferably 1%, in the coating vehicle with improved results.

EXAMPLE 4

Coating Antimicrobial Agents and Heparin or Dextran Sulfate on I.V. Catheters

It is sometimes important that certain medical devices possess bio-activity beyond antimicrobial effects. To this end, it has been found that other bio-active agents can be incorporated into the matrices without hampering the antimicrobial aspects.

As a preferred embodiment, polyurethane catheters were coated with a biomedical polyurethane coating vehicle containing 1% chlorhexidine+1% AgSD+0.2% heparin. The heparin imparts anti-coagulent effects to the catheter. Likewise, dextran sulfate was incorporated in the same quantities.

Table VII, below provides data showing that the addition of heparin to the coating vehicle does not interfere with antimicrobial activity of the coated device.

TABLE VII

Retention of Antibacterial Efficacy in Heparin-Coated Catheters

| | Retention of Antimicrobial Activity (Days) | |
|---|---|---|
| | With Heparin | Without Heparin |
| Triple lumen catheter | 6 | 6 |
| Single lumen catheter | 4 | 4 |

The testing was done in TSB culture as described above. The coating which was made as follows: 0.2 gm of heparin was dissolved in 2–3 cc of water to which 7 ml of ethyl alcohol was added. 3 gm of biomedical polyurethane, pellethane® 2363-80AE, was dissolved in 75 ml of THF and the heparin solution mixed therein. 1 gm of chlorhexidine acetate was dissolved in 15 ml of ethanol, after which 1 gm of AgSD was suspended therein. The antimicrobial agent solution was mixed with the polyurethane solution, and agitation maintained to insure a uniform suspension. The catheters were dipped in the solution, dried and tested. Coating can also be done in stages, i.e., a first coating of antimicrobial+matrix, followed by a second of heparin+matrix.

EXAMPLE 5

Arterial grafts of two commercially available types were provided with an antimicrobial coating in accordance with the invention. One was an expanded polytetrafluoroethylene (PTFE) sold under the Gortex® name as a reinforced expanded PTFE vascular graft 8 mm in diameter. The second was a 6 mm straight woven Dacron® arterial graft sold by Bard.

Short sections of each of these materials were coated with each of the following coating vehicles:

1. 1% PLA + 1% polyurethane + 1% CHA + 3% pipracil in $\frac{25\% \ NEP}{75\% \ THF}$ 2. 0.5% PLA + 0.5% polyurethane + 1% CHA + 3% pipracil in $\frac{25\% \ NEP}{75\% \ THF}$ 100 ml batches of these coating vehicles were prepared by dissolving 3 gm of pipracil in 20 cc of NEP. 1 gm of CHA was separately dissolved in 5 cc of NEP. The required amount, either 1 gm or 0.5 of polyurethane was dissolved in 50 cc of THF and the same amounts of PLA were dissolved in 25 cc of THF. The four solutions were then combined and thoroughly mixed to provide the coating vehicles.

The polyurethane used was Pellethane® 2363-80AE. The PTFE sections, because of their unique structure, contain a number of cavities or interstices which require either vigorous agitation or the application of a vacuum to the section in the presence of coating vehicle to insure that the coating vehicle penetrates and permeates the graft. The woven graft requires only simple agitation in coating vehicle to provide a good coating. Both products are then air dried.

A good adherent coating formed on the Dacron® graft. In the case of the PTFE graft, its characteristic surface refused to retain a surface coating. However, the coating composition was retained in the interstices, and, on drying, retained a coating composition having, by weight, one part biomedical polyurethane, one part PLA, one part CHA, and three parts pipracil in the case of coating 1, and 0.5 parts each of PLA and polyurethane, with one part CHA and three parts pipracil for coating 2.

The activity of the processed grafts are determined by the two types of bioassays described below:

Bioassay A—2 cm sections of graft are embedded in a 5% sheeps blood agar plate which were inoculated with $2 \times 10^4$ CFU *Staph. aureus*. Activity was determined by measuring the zone of inhibition. The graft sections were transferred to newly inoculated plates daily until antibacterial activity ceased.

Bioassay B—1 cm section of graft were soaked in 5 cc of trypticase soy broth (TSB) which was inoculated with $10^4$ CFU of *Staph. aureus*. If there was no turbidity after 24 hours incubation at 37° C., then the material was deemed to be bacteriostatic. The grafts were transferred to new TSB and inoculated daily.

| | | Results | | | |
|---|---|---|---|---|---|
| Bioassay A | | Zone of Inhibition (mm) | | | |
| Group | Days | 1 | 3 | 6 | 9 |
| PTFE (Formula 1) | | 23 | 19 | 16 | 12 |
| PTFE (Formula 2) | | 29 | 20 | 16 | 12 |
| Bard (Formula 1) | | 29 | 15 | 12 | 12 |
| Bard (Formula 2) | | 29 | 15 | 14 | 11.5 |
| Untreated Control | | 0 | | | |

Bioassay B

All processed groups show activity for more than 10 days.

Untreated Control showed heavy growth and turbidity after one day.

EXAMPLE 6

An expanded polytetrafluorethylene (PTFE) hernia patch was impregnated with an infection-resistant material comprising silver sulfadiazine and chlorhexidine acetate in a biodegradable matrix of poly(lactic acid) using the following method.

An impregnating vehicle was prepared by mixing 0.5% chlorhexidine acetate, 0.5% silver sulfadiazine and 1% poly(lactic acid), mw 44,000, in a solvent mixture comprising 95% ethanol and THF in the proportions of 10:90. The chlorhexidine acetate and PLA are in solution in this mixture; the silver sulfadiazine is in suspension.

An expanded PTFE hernia patch, 2×2 cm and having a thickness of about 0.5 cm was soaked for 5 minutes in the impregnating vehicle prepared above, with continuous stirring to maintain a uniform suspension. The patch was then removed from the suspension, air dried for about one minute and then placed in an oven at 40° C. for 24 hours.

The antibacterial efficacy of the patch was evaluated, utilizing Bioassay B described in Example 5 above. Several 1 $cm^2$ pieces were cut and soaked in TSB and kept in water bath shakers at 37° C. The TSB is changed daily and 4 pieces were removed at different intervals and tested for zone of inhibition. The results are given in the following table:

| Days of Soaking | Zone of Inhibition (mm) against *Staph. aureus* after 1 day |
| --- | --- |
| 0 | 24 |
| 1 | 22 |
| 3 | 20 |
| 6 | 20 |

EXAMPLE 7

Method of in situ Incorporation of Silver

Sulfadiazine and Chlorhexidine in Hernia Patch

The interstices of a hernia patch, which is made up of expanded PTFE, are too small for a sufficient amount of silver sulfadiazine (AgSD) molecules to enter. Therefore silver sulfadiazine is precipitated in situ by treating the patch with sodium sulfadiazine (NASD) and silver nitrate. The following methods were used to incorporate silver sulfadiazine and chlorhexidine acetate (CHA) into the interstices of a patch.

1. An expanded polytetrafluoroethylene (PTFE) hernia patch, 2×2 cm and having a thickness of about 0.5 cm is first soaked in:
   (a) a 95% ethanol solution of 0.5% silver sulfadiazine and 0.5% chlorhexidine acetate for 2–3 minutes, removed, dried for about one minute;
   (b) the patch is then soaked in 0.25% AgNO solution for 2–3 minutes, removed and air dried. The patch is then placed in an oven at 40° C. for 24 hours.
2. The procedure is the same as in 1, but the first solution contains 0.4% sodium sulfadiazine, 0.5% chlorhexidine acetate, and 1% PLA, mw 44,000, in a solvent comprising a 95% ethanol:THF mixture (10:90).

In an alternative to both the 1 and 2 methods, the first dipping step was done in $AgNO_3$ solution and then in the mixture of sodium sulfadiazine and chlorhexidine acetate.

Evaluation of Antibacterial Efficacy of Patches Coated by this Process

Following the bioassay method of Example 6, several 1 $cm^2$ pieces were cut and soaked in TSB and kept in water bath shakers. The TSB was changed daily and 4 pieces were removed at different intervals and tested for zone of inhibition.

| Coating Procedure | Zone of Inhibition (Days) | | |
| --- | --- | --- | --- |
| | 1 | 3 | 6 |
| Method A | | | |
| NaSD + CHA → $AgNO_3$ | 23 | 21 | 20 |
| $AgNO_3$ → NaSD + CHA | 22 | 21 | 20 |
| Method B | | | |
| NaSD + CHA + PLA → $AgNO_3$ | 22 | 20 | 19 |
| $AgNO_3$ → NaSD + CHA + PLA | 22 | 20 | 19 |

EXAMPLE 8

A coating vehicle for use in accordance with the present invention was prepared as follows:

1 gm of chlorhexidine acetate (CHA) was added to 5 cc of N-ethyl-2-pyrrolidone (NEP). The mixture was heated to 50°–60° C. and agitated in a Vortex® stirrer until the CHA dissolved.

10 cc tetrahydrofuran (THF) was then added to the CHA solution in NEP and the mixture thoroughly agitated to form a uniform solution.

3 gm of Pellethane® 2363-80AE of the Dow Chemical Co. was added to 50 cc of THF. The mixture was warmed to about the boiling point of THF, 65°–70° C., and stirring with a Vortex® stirrer was continued until the polyurethane was dissolved.

1 gm of silver sulfadiazine (AgSD) micronized powder was suspended in 35 cc of THF and vigorously agitated in a Vortex® stirrer to form a uniform suspension. The CHA solution in NEP and THF prepared above was then combined with the polyurethane solution and agitated to form a clear solution. As a last step in preparing the coating vehicle, the AgSD suspension in THF was added and the entire mixture agitated to maintain a uniform suspension. Thus was provided a coating vehicle containing 1% CHA and 1% AgSD as antimicrobial agents, together with 3% of the biomedical polyurethane. The solvent in this case was a mixture of solvents comprising 5% NEP and 95% THF. The CHA was in solution in the coating vehicle, while the AgSD was in uniform suspension.

The coating vehicle prepared above was used to coat an I.V. catheter fabricated of Pellethane® 2363-90A. The catheter was dipped in the coating vehicle while the vehicle was being continuously agitated to insure a uniform suspension. The coated catheter was then dried. A tightly adherent coating on the catheter was thus provided.

EXAMPLE 9

Synergism of Silver Sulfadiazine (AgSD)

and Chlorhexidine (CHA)

The results of experiments described below indicate that coating silver salts, preferably sulfadiazine, and chlorhexidine or its salts onto medical devices imparts prolonged antibacterial activity. In addition, in vitro studies show that chlorhexidine exhibits a synergistic effect when combined with silver sulfadiazine and thus increases the antimicrobial spectrum. AgSD+CHA also kills 99.9% of the bacterial population faster than chlorhexidine alone which is important for its use in medical gloves and condoms. Furthermore, when wound dressings (Epilock® dressings) coated with silver sulfadiazine and chlorhexidine were tested for zone of inhibition against a mixed culture of *Staph. aureus* and *Ps. areuginosa*, a synergistic effect was observed.

Analytical Procedures for Determinating the

Drug Content and Rate of Release from Devices

Determination of silver (Ag), sulfadiazine (SD) and chlorhexidine acetate (CHA) values is performed as follows:

Silver and SD

The devices (catheters) were coated with radioactive silver sulfadiazine ($^{110}$AgSD) and after measuring the initial radioactivity they were suspended in culture media or saline. The catheters were transferred daily to fresh media or saline and the radioactivity remaining in the catheter segments were measured using a Nuclear Chicago 1185 automated gamma counter. The amount of SD released was measured by determining the SD content of the media using a calorimetric method (Bratton-Marshal Test).

Initial levels of SD in the catheters were determined by extracting the SD from the catheters with 0.2 molar nitric acid.

CHA

CHA levels are determined spectrophotometrically (231 nm and 254 nm) using a Hitachi® 2000 double beam UV/VIS system. Initial levels were measured by extracting the CHA from the catheter using warm ethanol. The CHA released into the media was also measured spectrophotometrically. These spectrophotometric levels were corroborated by bioassay such as zone of inhibition tests.

In vitro Studies

Different concentrations of silver sulfadiazine or chlorhexidine alone or in combinations were added to mixed cultures of *Ps. areuginosa* and *Staph. aureus* ($10^5$ CFU of each organism) in 2 ml trypticase soy broth (TSB) and incubated along with control cultures. 0.1 ml aliquots were removed from these cultures and diluted to 10 ml (1 to 100 dilution) at 10 minutes, 20 minutes and 40 minutes. 0.2 ml of these diluted samples were subcultured on blood agar plates and colony counts were made 24 hours post incubation. The results are given the following Table VIII.

TABLE VIII

| | | Bacterial Inhibition | | |
|---|---|---|---|---|
| | Concen- | Colony Forming Units (CFU) | | |
| Antimicrobial Agent | tration (μmole/2 ml) | 10 | 20 | 40 minutes |
| None | 0 | >$10^6$ (S&P) | >$10^6$ (S&P) | >$10^6$ (S&P) |
| AgSD | 1.0 | $2 \times 10^5$ (S&P) | $1 \times 1 \times 10^5$ (S&P) | $1.2 \times 10^5$ (S&P) |
| CHA | 1.0 | $1 \times 10^3$ (S) | 0 | 0 |
| AgSD + CHA | 1.0 + 1.0 | 0 | 0 | 0 |
| AgSD | 0.5 | >$10^6$ (S&P) | >$10^6$ (S&P) | >$10^6$ (S&P) |

TABLE VIII-continued

| | | Bacterial Inhibition | | |
|---|---|---|---|---|
| | Concen- | Colony Forming Units (CFU) | | |
| Antimicrobial Agent | tration (μmole/2 ml) | 10 | 20 | 40 minutes |
| CHA | 0.5 | $1 \times 10^5$ (S) | $3.7 \times 10^4$ (S) | $2 \times 10^2$ (S) |
| AgSD + CHA | 0.5 + 0.5 | 0 | 0 | 0 |

S&P = *Staph. aureus* and *Ps. areuginosa*
S = *Staph. aureus*

The results show:
1. chlorhexidine acts rapidly, and by 20 minutes kills the organisms present;
2. silver sulfadiazine exhibits steady and prolonged suppression of growth (also see the example relating to wound dressings below); and
3. AgSD+CHA demonstrate a marked improvement over the individual results as there is even a more rapid kill (10 minutes), and prolonged suppression.

The results clearly show a fast and prolonged and synergistic antibacterial activity for the combination of AgSD+CHA, exhibiting far superior results than by using each such antimicrobial agent alone.

EXAMPLE 10

Synergistic results are also found when other silver salts are combined with chlorhexidine, as shown in Table IX, below.

TABLE IX

Synergistic Effect of Silver Compounds and Chlorhexidine against *Staph. aureus*, in vitro

| Drug Concentration | Colony Count (Minutes) | |
|---|---|---|
| in Culture | 20 | 60 |
| 100 μg silver sulfadiazine | 9,500 | 8,000 |
| 100 μg silver oxide | 7,500 | 8,000 |
| 100 μg silver carbonate | 9,200 | 6,000 |
| 100 μg chlorhexidine acetate | 6,250 | 4,000 |
| 50 μg silver sulfadiazine + 50 μg chlorhexidine acetate | 4,800 | 0 |
| 50 μg silver oxide + 50 μg chlorhexidine acetate | 3,700 | 0 |
| 50 μg silver carbonate + 50 μg chlorhexidine acetate | 4,300 | 0 |
| 100 μg silver nitrate | 10,500 | 11,000 |
| 100 μg chlorhexidine, water insoluble | 6,000 | 3,000 |
| 50 μg silver nitrate + 50 μg chlorhexidine, water insoluble | 100 | 0 |
| CONTROL | 16,000 | 15,000 |

For Table IX, 3 ml of TSB culture of *Staph. aureus* ($10^4$ CFU/ml) containing the drug were incubated for one hour at 37° C. and the colony counts measured. The results achieved further show the synergistic interaction between silver salts and chlorhexidine salts in causing complete suppression of growth by 60 minutes, whereas each anti-bacterial agent, alone, showed only partial suppression.

EXAMPLE 11

Methods for the Preparation of Coated Medical Devices and Evaluation of Antibacterial Activity Certain medical devices are comprised of materials not fully compatible with biomedical polyurethane as a coating vehicle, requiring, for compatible matrices, the use of a biomedical silicone, with or without a biodegradable polymer such as poly(lactic acid) (PLA).

Method A

Chlorhexidine diacetate is mixed uniformly in 1% to preferably 5%, silicone solution in ethyl acetate, or silicone solution containing .2 to 2%, preferably 0.5% or 1% poly(lactic acid), molecular weight 2000. The medical device is dipped for 10 seconds in this suspension which is kept at room temperature. The silicone used was Silastic® Medical Adhesive Silicone Type A.

Method B 0.5 to 10% chlorhexidine diacetate is mixed uniformly in 1% PLA solution (equal amounts of 2,000, 44,000, 100,000 and 300,000 molecular weight PLA) in ethyl acetate. This antimicrobial suspension is kept at 50° C. in a water bath and mixed continuously. The medical device to be coated is dipped for one minute in this suspension, removed and dried.

In both of the above methods, other antimicrobial agents can also be used either singly or in combination as shown below.

Coating of Latex Gloves

The fingers of latex medical gloves were washed, dried and dip-coated with (a) chlorhexidine acetate (CHA), (b) CHA and silver sulfadiazine (AgSD), and (c) AgSD using antimicrobial suspensions prepared by Method A above. The silicone used in this test was a mixture of equal parts by weight of Silastic® Medical Adhesive Silicone Type A, and MDX-4-4159, a fluid comprising equal parts of an active polydimethyl siloxane and a solvent therefor comprising mixed aliphatic and isopropanol solvents. The PLA employed was a poly(L-lactic acid) procured from Polysciences, Inc., Warrington, Pa., having various molecular weights. PLA-2000 has a molecular weight of 2000. The suspension had the following composition:
1. 10% CHA+10% silicone+0.5% PLA-2000
2. 5% CHA+5% AgSD+10% silicone+0.5% PLA-2000
3. 10% silver sulfadiazine+10% silicone+0.5% PLA-2000

The antibacterial efficacy was tested against a mixed culture of *Pseudomonas aeruginosa* and *Staphylococcus aureus* having $10^4$ CFU of each per 2 ml of culture.

The coated fingers were suspended in culture tubes and 2 ml of 5% bovine albumin solution containing the mixed bacterial culture were added to it and incubated at 37° C. The rate of killing was determined by taking aliquots at 10, 20 and 40 minutes and subculturing on blood agar plates for colony counts. The results are given in Table X below.

TABLE X

| | Colony Counts of *Staph. aureus* and *Ps. aeruginosa* (Colony Forming Units - CFU/2 ml Culture) | | | | | |
|---|---|---|---|---|---|---|
| Antimicro- | 10 Minutes | | 20 Minutes | | 40 Minutes | |
| bial Agent on Gloves | *Staph. aureus* | *Ps. aer.* | *Staph. aureus* | *Ps. aer.* | *Staph. aureus* | *Ps. aer.* |
| CHA | $8 \times 10^3$ | 0 | $2 \times 10^3$ | 0 | 0 | 0 |
| CHA + AgSD | $4 \times 10^3$ | 0 | 0 | 0 | 0 | 0 |
| AgSD | $1 \times 10^4$ | $1.2 \times 10^4$ | $5 \times 10^3$ | $8 \times 10^3$ | $4 \times 10^3$ | $5 \times 10^3$ |
| None (Control) | $1 \times 10^4$ | $1 \times 10^4$ | $1 \times 10^4$ | $8 \times 10^3$ | $2 \times 10^4$ | $8 \times 10^3$ |

These results demonstrate improved and sustained suppression of bacterial growth when using the combination of CHA+AgSD on gloves.

EXAMPLE 12

Coating of Urinary Catheters and Evaluation of Antibacterial Activity.

Using the methods described in A and B in Example 11 above, latex urinary catheters were coated with a coating vehicle containing Silastic® Medical Adhesive Silicone Type A in Method A and PLA in Method B, both having various amounts of chlorhexidine and/or silver sulfadiazine and 2.0 cm segments were soaked in either 5 ml trypticase soy broth (TSB or 5 ml urine inoculated with a mixture of $10^4$ organisms of *Staph. epi* and *E. coli*. After 24 hours of incubation at 37° C., the media was subcultured to quantitatively determine bacterial levels. The segments were then transferred to fresh media which was re-inoculated. This procedure was continued until the urinary catheter segments no longer presented antibacterial activity. The results, showing significant retention of bio-active material are given in Table XI below.

TABLE XI

Retention of Antibacterial Activity of Coated Urinary Catheters

| Antimicrobial Agent on Urinary Catheters | % Antimicrobial Agent in Coating Solution | Retention (Days) In Presence of Urine | Retention (Days) In Presence of TSB | Nutrient Agar Plate |
|---|---|---|---|---|
| Method A - CHA | 10 | 5 | 4 | >7 |
| Method A - CHA | 5 | 4 | 3 | 5 |
| Method A - AgSD | 5 | 2 | 2 | 5 |
| Method A - CHA + AgSD | 5 + 5 | 3 | 3 | >7 |
| Method A - None (Control) | 0 | 0 | 0 | 0 |
| Method B - CHA | 10 | 6 | 4 | >7 |
| Method B - CHA | 5 | 4 | 3 | 5 |
| Method B - AgSD | 4 | 2 | 2 | 5 |
| Method B - CHA + AgSD | 5 + 5 | 3 | 3 | 6 |
| Method B - None (Control) | 0 | 0 | 0 | 0 |

CHA = chlorhexidine acetate
AgSD = silver sulfadiazine

EXAMPLE 13

Antibacterial Efficacy of Coatings Containing Chlorhexidine Acetate and Biodegradable Polymers on Polyurethane I.V. Catheters Using the method described as Method B in Example 11 above, I.V. catheters fabricated of Pellethane® 2363-80AE, a biomedical polyurethane, were coated with a coating vehicle which, in a first series, contained 1% chlorhexidine acetate in a solvent comprising 10% of 95% ethanol and 90% ethyl acetate. A second series used a coating vehicle containing 1% chlorhexidine acetate and 3% of Pellethane® 2363-80AE in a solvent comprising 10% of 95% ethanol and 90% of THF. The third series used a coating vehicle comprising 1% chlorhexidine acetate, 5% of Silastic® Type A Medical Adhesive, a polymethyl siloxane, and 2% of MDX 4-4159, a silicone comprising 50% of an amino functional polydimethyl siloxane copolymer and 50% mixed aliphatic and isopropanol solvents. In addition, each of the three series contained a biodegradable polymer at a level of 1%; the polymers were obtained from Polyscience.

The procedure described in Example 12 was used to test 2.0 cm segments of the coated catheter. The results obtained are summarized in the following table:

| Biodegradable Polymers | 1-day Zone of Inhibition (mm) CHA Alone | CHA with Polyurethane | CHA with Silicone |
|---|---|---|---|
| Poly(lactic acid), mw 100,000 | 21 | 21 | 20 |
| Polycaprolactone | 20 | 19 | 19 |
| Polyhydroxybutyric acid, mw 30,000 | 20 | 21 | 21 |

The zone of inhibition was tested on blood agar culture plates seeded with *Staph. aureus* ($10^4$ organisms).

EXAMPLE 14

Multicoating

At times, urinary catheters or intravenous catheters coated with biomedical polyurethane and bio-active agents or silicone (with or without PLA) and bio-active agents are found to possess surface characteristics not fully desirable. To overcome this problem, the invention further comprises the provision of a second (or more) coatings.

It has been found that a second coating applied over the biomedical polyurethane coating by spraying, dipping or otherwise, of between 0.5 to 5% of a silicone fluid such as the MDX4-4195 described in Example 11 in solution in hexane, preferably 2%, after drying, renders the coated medical device, especially a catheter, smoother in texture, with improved lubricity and improved retention characteristics, as shown in Table XII.

TABLE XII

Retention of Antibacterial Efficacy in Presence of TSB Culture

| Drug Coated Catheter Sample | Bacterial Growth Days 1 | 2 | 3 | 4 | 5 | 6 | 7 |
|---|---|---|---|---|---|---|---|
| MDX Coating | | | | | | | |
| 1 | 0 | 0 | 0 | 0 | 0 | 0 | 0 |
| 2 | 0 | 0 | 0 | 0 | 0 | 0 | 0 |
| 3 | 0 | 0 | 0 | 0 | 0 | 1+ | 2+ |
| 4 | 0 | 0 | 0 | 0 | 0 | 0 | 0 |
| 5 | 0 | 0 | 0 | 0 | 1+ | 2+ | 4+ |
| 6 | 0 | 0 | 0 | 0 | 0 | 0 | 1+ |
| 7 | 0 | 0 | 0 | 0 | 0 | 0 | 1+ |
| 8 | 0 | 0 | 0 | 0 | 0 | 0 | 1+ |
| 9 | 0 | 0 | 0 | 0 | 0 | 0 | 1+ |
| No MDX Coating | | | | | | | |
| 1 | 0 | 0 | 0 | 0 | 0 | 1+ | |
| 2 | 0 | 0 | 0 | 0 | 1+ | 1+ | |
| 3 | 0 | 0 | 0 | 0 | 1+ | 1+ | |
| 4 | 0 | 0 | 0 | 0 | 1+ | 1+ | |
| 5 | 0 | 0 | 0 | 0 | 1+ | 1+ | |
| 6 | 0 | 0 | 0 | 0 | 0 | 1+ | |
| Control Catheter No Antimicrobial Agent | Heavy (++) | | | | | | |

2 cm segments of drug coated catheters (AgSD+CHA) in a biomedical polyurethane coating agent of 3% Pellethane® 2363-80AE in a solvent of THF+ethanol or DMAC+ethylacetate were coated with a second coating by applying hereto a 2% solution of MDX4-4195 in hexane. After thorough drying to remove solvent, the segments were suspended in 5 ml TSB containing $10^4$ *Staph. aureus* and incubated at 37° C. Every 24 hours, for seven days, the bacterial growth in the culture was measured by visual turbidity and colony counts and the catheter segment was transferred to fresh culture and the experiment repeated.

Bacterial growth was properly suppressed for seven days. In addition, the catheters possessed smoother surfaces. This multicoating process can also use PLA in the first coating, and over a range of 0 2 to 2%, preferably 1% in the coating vehicle with improved results.

EXAMPLE 15

Coating Antimicrobial Agents and Heparin or Dextran Sulfate on I.V. Catheters

It is sometimes important that certain medical devices possess bio-activity beyond antimicrobial effects. To this end, it has been found that other bio-active agents can be incorporated into the matrices without hampering the antimicrobial aspects.

As a preferred embodiment, polyurethane catheters were coated with a biomedical polyurethane coating vehicle containing 1% chlorhexidine+1% AgSD+0.2% heparin. The heparin imparts anti-coagulent effects to the catheter. Likewise, dextran sulfate was incorporated in the same quantities.

Table XIII, below provides data showing that the addition of heparin to the coating vehicle does not interfere with antimicrobial activity of the coated device.

TABLE XIII

Retention of Antibacterial Efficacy in Heparin-Coated Catheters

| | Retention of Antimicrobial Activity (Days) | |
|---|---|---|
| | With Heparin | Without Heparin |
| Triple lumen catheter | 6 | 6 |
| Single lumen catheter | 4 | 4 |

The testing was done in TSB culture as described above. The coating which was made as follows: 0.2 gm of heparin was dissolved in 2–3 cc of water to which 7 ml of ethyl alcohol was added. 3 gm of biomedical polyurethane, Pellethane® 2363-80AE, was dissolved in 75 ml of THF and the heparin solution mixed therein. 1 gm of chlorhexidine acetate was dissolved in 15 ml of ethanol, after which 1 gm of AgSD was suspended therein. The antimicrobial agent solution was mixed with the polyurethane solution, and agitation maintained to insure a uniform suspension. The catheters were dipped in the solution, dried and tested. Coating can also be done in stages, i.e., a first coating of antimicrobial+matrix, followed by a second of heparin +matrix.

EXAMPLE 16

Coating of Wound Dressings

Johnson and Johnson gauze dressings and Epilock® dressings manufactured by Dermalock Medical Corporation were coated with antimicrobial agents. These coated dressings were prepared using methods (a) and (b) above. The zone of inhibition was tested against a mixture of *Ps. aeruginosa* and *Staph. aureus* cultures on nutrient agar plate.

TABLE XIV-A

Antibacterial Activity of Johnson and Johnson Dressings

| Antimicrobial Agent in Dressings | % Antimicrobial Agent in Coating Solution | Zone of Inhibition (mm) | |
|---|---|---|---|
| | | 1 day | 2 day |
| Method A - CHA | 10 | 27 | 20 |
| Method A - AgSD | 5 | 25 | 18 |
| Method A - CHA + AgSD | 5 + 5 | 25 | 20 |
| None (Control) | 0 | 0 | 0 |

TABLE XIV-B

Antibacterial Activity of Epilock ® Dressings

| Antimicrobial Agent in Dressings | % Antimicrobial Agent in Coating Solution | Zone of Inhibition (mm) | | | | |
|---|---|---|---|---|---|---|
| | | 1 | 2 | 3 | 4 | 5 Days |
| Method A - CHA | 10 | 28 | 28 | 43 | 40 | 25 |
| Method A - AgSD | 5 | 30 | 35 | 43 | 27 | 28 |
| Method A - CHA + AgSD | 5 + 5 | 34 | 45 | 43 | 27 | 34 |
| Method B - CHA | 10 | 27 | 21 | 22 | 24 | 24 |
| Method B - AgSD | 5 | 31 | 35 | 35 | 0 | 0 |
| Method B - CHA + AgSD | 5 + 5 | 38 | 28 | 37 | 30 | 25 |
| None (Control) | 0 | 0 | 0 | 0 | 0 | 0 |

These results demonstrate the improvement in using the synergistic combination, as well as the general efficacy of the process. Wound dressings may also be provided with an adhesive on one side (to attach to the wound). In such cases, the invention further comprises seven methods of application of the antimicrobial agent:

1. Suspending the antimicrobial agents, preferably silver sulfadiazine and chlorhexidine in the quantities of 1–5% total, in a carrier that evaporates but does not solubilize the adhesive, instead leaving the adhesive intact, e.g., an alcohol, and spraying the agent-containing carrier upon the dressing, or dipping the dressing into the agent-containing carrier solution.
2. Placing the antimicrobial agents in a solution containing silicone or polyurethane (preferably 1%) and a carrier (preferably ethyl acetate, THF or $H_2O$ and spraying it upon the dressing, or dipping the dressing into it.
3. Applying powdered antimicrobial agents (preferably silver sulfadiazine and chlorhexidine) to the adhesive in microlayers that do not eliminate adhesion.
4. Admixing powdered antimicrobial agents with adhesive prior to application.
5. Adding a biodegradable material containing antimicrobial agents to the adhesive to provide controlled-release through degradation.
6. Providing spots containing antimicrobial agents, surrounded by adhesive.
7. Providing a biodegradable or nonbiodegradable adhesive composition containing antimicrobial agents.

EXAMPLE 17

Method of Coating Antimicrobial Agents on the Surface of Latex Gloves

During Automated Manufacturing Process

The invention is especially useful in the automated manufacturing of gloves. There are two methods found useful in the coating of the combination of chlorhexidine and silver sulfadiazine.

Method 1

Latex gloves are typically manufactured by (1) dipping a form in molten latex, (2) removing the latex form and transferring it to a dryer, (3) removing the form with attached glove from the dryer and immediately spraying it with a dusting powder, as it cools. A suspension of silver sulfadiazine in alcohol or water in an aqueous silicone latex emulsion (1–5% by volume)+chlorhexidine (1–5%+dusting powder (2–10%) is sprayed on the gloves as the gloves are dispensed from the dryer at 120° C. At this temperature, the antimicrobial agents and the dusting powder particles adhere well to the soft and/or semi-molten surfaces of the gloves. The antimicrobial activity is not in any way altered as a consequence of this process, because of the falling temperature of the gloves, as they cool. This is a preferred procedure in cases where presence of other organic solvents in the coating process is a concern to the manufacturer.

Method 2

Sterile corn starch-based dusting powder is admixed with silver sulfadiazine (1–5% by weight) and chlorhexidine (1–5% by weight) in powdered form, and the mixture is sprayed on the gloves as they are dispensed from the dryer at 120° C., and start to cool. The dusting powder with enhanced antimicrobial activity remains with the gloves.

EXAMPLE 18

Preparation of Infection-Resistant Devices with

Silver Sulfadiazine and Chlorhexidine Using a Mixture of Silicones as the Polymeric Coating Agent In order to obtain a coating which is lubricious, adheres well to the catheter and also releases the drug in a controlled dosing manner, a mixture of Silastic® Medical Adhesive Type A, a polydimethyl siloxane, and MDX-4-4159, a fluid silicone comprising equal parts of an amino functional polydimethyl siloxane copolymer and a mixed aliphatic and isopropanol solvent were used as the polymeric coating agents. Silastic® Medical Adhesive Silicone Type A alone forms an undesirable surface, while the MDX-4-4159 alone does not form an adherent film on the surface. However, use of a mixture of these two silicones in 1:1 proportions gives a coating vehicle which forms a film with the desired biocompatible characteristics. The Silastic® functions as the bonding agent whereas the MDX-4-4159 imparts lubricity to the surface. In addition, the MDX-4-4159 prolongs the release of the antimicrobial agent.

The coating agent was prepared by dispersing 2.5 ml of Silastic® Medical Adhesive Type A in 55 ml of THF to which 2.5 ml of MDX-4-4159 is added. 4 g of Ag SD are suspended in 30 ml and 2g of CHA are dissolved in 10 ml of ethanol. The AgSD suspension is mixed with the silicone dispersons and finally the CHA solution is added dropwise while the preparation is agitated. Either 5% NEP or 5% DMAC can be substituted for ethanol in the above formulation.

The coating agent prepared above was used to apply a coating on catheters fabricated from silicone, polyurethane and latex substrates. The coatings were applied by dipping and drying, as described in Example 2. Results are given in Table XV below.

TABLE XV

Antibacterial Efficacy of Polyurethane
I.V. Catheters and Latex or Silicone Urinary
Catheters Coated with A silicone Matrix

| Catheter Type | Drug in Catheter | Days of Activity* |
|---|---|---|
| Polyurethane I.V. | CHA | 2 |
| Polyurethane I.V. | AgSD + CHA | 4 |
| Latex urinary | AgSD | 2 |
| Latex urinary | AgSD + CHA | 4 |
| Silicone urinary | AgSD | 3 |
| Silicone urinary | AgSD + CHA | 4 |

*Determined via Bioassay A. Inoculum used to assay urinary catheter is a $10^4$ CFU of a 1:1 mixture of *Staph. epi* and *E. coli*; $10^4$ CFU of *Staph. aureus* is used to challenge the I.V. catheter.

EXAMPLE 19

Silver sulfadiazine and chlorhexidine acetate were added over a range of proportions to cultures of *Staph. aureus* containing $10^5$ colony forming units (CFU) in 2 ml trypticase soy broth (TSB) and the cultures were incubated along with control cultures at 37° C. 0.1 ml aliquots were removed from these cultures and diluted to 10 ml, a 1:100 dilution after one hour. 0.2 ml of these diluted samples were subcultured on blood agar plates and colony counts were made 24 hours post incubation. The results are given in the following Table XVI.

TABLE XVI

Synergism of Different Combinations
of Silver Sulfadiazine (AgSD)
and Chlorhexidine (CHA) against *Staph. aureus*

| Concentration µg/2 ml AgSD + CHA | | Bacterial Inhibition Colony Forming Units After 1 Hour |
|---|---|---|
| 0 | 100 µg | 650 |
| 25 µg | 75 µg | 100 |
| 50 µg | 50 µg | 150 |
| 75 µg | 25 µg | 100 |
| 87.5 µg | 12.5 µg | 150 |
| 100 µg | 0 | 3,100 |
| 0 | 0 | 4,100 |

EXAMPLE 20

Coating of Latex Gloves

The fingers of latex gloves were washed and dried. They were then sprayed with a fine mist spray of a coating solution to provide a uniform coating of solution on the glove surface, sufficient to provide complete wetting thereof without runoff. The coating solutions were prepared by dissolving 1% Silastic® Medical Adhesive Type A and 1% of the silicone MDX4-4159 in ethyl acetate, followed by dissolving and dispersing the chlorhexidine acetate and silver sulfadiazine, respectively, therein. The coating was air dried for 24 hours and the gloves tested using the following test:

Treated glove fingers were draped over the tops of culture tubes with the treated side with sprayed on coating forming the inside of the cup shape. Then 3.0 ml of TSB containing $10^4$ colony forming units of *Staph. aureus* was dispensed in each finger and all placed in a water bath shaker at 37° C. Samples were removed at 15 minutes, 1 hour, hours, and 4 hours, diluted 1–10, and the solution plated on blood agar in 2.0 ml amounts.

The results of the test are summarized in the following Table XVII.

TABLE XVII

Antibacterial Efficacy of Drug Coated Gloves against *Staph. aureus*

| Drug in Coating Solution | Colony Counts in Culture | | | |
|---|---|---|---|---|
|  | 15 min. | 1 hour | 2 hours | 4 hours |
| None (Control) | 12,000 | 15,000 | 20,000 | 50,000 |
| Chlorhexidine (1%) | 100 | 0 | 0 | 0 |
| Silver Sulfadiazine (2%) | 3,300 | 200 | 0 | 0 |
| Silver Sulfadiazine (1%) + Chlorhexidine (1%) | 0 | 0 | 0 | 0 |

It is noted that the gloves coated according to this procedure were flexible and met all other requirements for high quality latex gloves.

EXAMPLE 21

The fingers of latex gloves were washed, dried, and sprayed with a fine mist of a coating solution to provide a uniform coating of solution on the glove surface, sufficient to provide complete wetting thereof without runoff. The coating solutions were prepared by dissolving 1% Silastic® Medical Adhesive Type A and 1% of the silicone MDX4-4159 in ethyl acetate, followed by dissolving or dispersing the chlorhexidine and silver sulfadiazine respectively therein. The coating was air dried for 24 hours and the gloves tested using the following test:

Treated glove fingers were draped over the tops of culture tubes with the treated side with sprayed on coating forming the inside of the cup shape. Then 3.0 ml of TSB containing $10^3$ colony forming units of *Candida albicans* was dispensed in each finger and all placed in a water bath shaker at 37° C. Samples were removed at 15 minutes, 1 hour, 2 hours, and 4 hours. They were diluted 1–10 and plated on blood agar in 2.0 ml amounts.

The results of the test are summarized in the following Table XVIII.

TABLE XVIII

Antibacterial Efficacy of Drug Coated Gloves against *Candida albicans*

| Drug in Coating Solution | Colony Counts in Culture | | | |
|---|---|---|---|---|
|  | 15 min. | 1 hour | 2 hours | 4 hours |
| None (Control) | 1,400 | 2,000 | 4,000 | 6,000 |
| Chlorhexidine (1%) | 75 | 0 | 0 | 0 |
| Silver sulfadiazine (2%) | 1,650 | 1,500 | 1,500 | 2,200 |
| Silver sulfadiazine (1%) + Chlorhexidine (1%) | 0 | 0 | 0 | 0 |

As in Example 20, the gloves coated according to this procedure were flexible and met all requirements for high quality latex gloves.

EXAMPLE 22

The fingers of latex gloves were washed and dried. They were then sprayed with a fine mist spray of the coating solution in runs 1–3 below to provide a uniform coating of solution on the glove surface, sufficient to provide complete wetting without runoff, after which the gloves were dried for hours. In run 4, the powder was blown on to the glove to form a uniform coating.

The coating compositions were prepared having the following ingredients:

1. 1% MDX4-4159+1% Silastic® Medical Adhesive Type A+1% CHA+1% AgSD+2% starch-based dusting powder in ethyl acetate.
2. 1% CHA +1% AgSD+2% dusting powder in ethanol.
3. 1% chlorhexidine gluconate (CHG)+1% AgSD+2% dusting powder in ethanol.
4. A mixture of CHA+AgSD+dusting powder in equal weight ratios.

The coated gloves were tested, following the procedure set forth in Example 16 above. The results are given in Table XIX.

TABLE XIX

Antibacterial Efficacy of Drug Coated Gloves against *Staph. aureus*

| Coating Solution | Colony Counts in Culture | |
|---|---|---|
|  | 15 min. | 1 hour |
| 1 | 0 | 0 |
| 2 | 0 | 0 |
| 3 | 0 | 0 |
| 4 | 0 | 0 |
| None (Control) | 12,000 | 15,000 |

It is noted that other medical gloves, including surgical and examination gloves, fabricated from other materials such as polyurethane, polyethylene, polypropylene, and polyvinyl acetate, may be coated following the process of this invention.

It is further noted that in both the dry powder process and the so-called wet powder process using a vehicle such as ethanol, the antimicrobial powders and dusting powders may be applied separately, and in any sequence.

EXAMPLE 23

This example illustrates the coating of medical gloves with a coating composition containing an aqueous silicone emulsion.

15 grams of a starch-based dusting powder is suspended in 50 ml of deionized water. The suspension is then mixed with 44.5 ml of deionized water in which 2 grams of micronized silver sulfadiazine is suspended. To this mixture is added 0.5 cc of L.E. 46, a silicone emulsion containing 35% dimethyl siloxane, sold by Dow Corning Company. Finally, 5 cc of a 20% chlorhexidine gluconate in water is added and the mixture stirred to maintain a uniform suspension.

Washed latex glove fingers are dipped into the mixture and air dried for one minute to provide an adherent, infection-resistant, coating.

EXAMPLE 24

Latex urinary catheters were provided with coatings including a series of antimicrobial agents. A coating solution was prepared containing 6% Dow Pellethane® 80AE in solvent comprising 5% NEP and 95% THF. The catheters were dipped in the solution to provide a uniform coating, and dried for 24 hours to remove the solvent. When used alone, the Ag salt was used at a 5% level. When a combination of agents were used, the silver salt was at a 2% level, as was the CHA. All silver salts were very finely divided, either by grinding in a mortar and pestle, or by purchase of micronized grade materials. Three 1 cm segments of each catheter were placed in the center of blood agar plates seeded with $10^4$ CFU of a 1:1 mixture of *Staph. epi* and *E. coli*, one section to each plate, and the zone of inhibition was measured after incubation at 37° C. for 24 hours. The results are given in the following Table XX.

TABLE XX

Antibacterial Efficacy of Drug Coated Urinary Catheters against *Staph. epi* and *E. coli*

| Drug on Catheter | Days | 1 | 2 | 3 | 4 | 5 | 6 |
|---|---|---|---|---|---|---|---|
| Chlorhexidine (CHA) | | 18 | 23 | 15 | 16 | 15 | 14 |
| Silver acetate | | 12 | 13 | 12 | 12 | 12 | 11 |
| Silver acetate + CHA | | 20 | 21 | 14 | 14 | 12 | 12 |
| Silver benzoate | | 13 | 12 | 10 | 11 | 11 | 12 |
| Silver benzoate + CHA | | 18 | 20 | 12 | 13 | 13 | 14 |
| Silver carbonate | | 13 | 12 | 12 | 12 | 12 | 13 |
| Silver carbonate + CHA | | 20 | 23 | 19 | 12 | 13 | 13 |
| Silver iodate | | 10 | 0 | 0 | 0 | 0 | 0 |
| Silver iodate + CHA | | 18 | 20 | 15 | 14 | 14 | 15 |
| Silver laurate + CHA | | 22 | 24 | 19 | 18 | 18 | 17 |
| Silver protein | | 10 | 0 | 0 | 0 | 0 | 0 |
| Silver protein + CHA | | 26 | 26 | 15 | 16 | 16 | 17 |
| Silver palmitate + CHA | | 26 | 26 | 23 | 18 | 18 | 18 |
| Silver chloride | | 11 | 6 | 6 | 10 | 10 | 10 |
| Silver chloride + CHA | | 20 | 15 | 14 | 15 | 15 | 15 |
| Silver oxide | | 14 | 12 | 11 | 12 | 12 | 12 |
| Silver oxide + CHA | | 22 | 25 | 15 | 14 | 15 | 15 |
| Silver sulfadiazine | | 8 | 8 | 7 | 10 | 10 | 10 |
| Silver sulfadiazine + CHA | | 20 | 15 | 15 | 15 | 16 | 16 |
| Silver tannate + CHA | | 20 | —* | — | — | — | — |

*Experiment discontinued after 1 day because of poor quality coating.

EXAMPLE 25

I.V. catheters fabricated of Pellethane® 2363-90A were provided with coatings including a series of antimicrobial agents. A coating solution was prepared containing 6% Dow Pellethane® 2363-80AE and the drug in a solvent comprising 5% N-ethyl-2-pyrrolidone (NEP) and 95% tetrahydrofuran (THF). When used alone, the Ag salt was used at a level of 5%. When combined with CHA, each was used at a level of 2%. The catheters were dipped in the solution to provide a uniform coating on the device, and thereafter allowed to dry for 24 hours to remove the solvent.

Three 1 cm segments of each catheter were placed in the center of blood agar plates seeded with $10^4$ CFU of *Staph. aureus*, one section to a plate, and the zone of inhibition was measured after 24 hours at 37° C. Results, expressed as the average of 3 determinations, are given in the following Table XXI.

TABLE XXI

Antibacterial Efficacy of Drug Coated I.V. Catheters against *Staph. aureus*

| | Zone of Inhibition (mm) | | | | |
|---|---|---|---|---|---|
| Drug on Catheter | 1 | 2 | 3 | 4 | 5 |
| Chlorhexidine (CHA) | 15 | 12 | 12 | 9 | 9 |
| Silver acetate | 10 | 8 | 10 | 9 | 8 |
| Silver acetate + CHA | 18 | 11 | 11 | 14 | 11 |
| Silver benzoate | 12 | 8 | 11 | 10 | 12 |
| Silver benzoate + CHA | 18 | 11 | 25 | 13 | 13 |

TABLE XXI-continued

Antibacterial Efficacy of Drug Coated I.V. Catheters against *Staph. aureus*

| | Zone of Inhibition (mm) | | | | |
|---|---|---|---|---|---|
| Drug on Catheter | 1 | 2 | 3 | 4 | 5 |
| Silver carbonate | 11 | 7 | 10 | 10 | 10 |
| Silver carbonate + CHA | 17 | 12 | 17 | 13 | 13 |
| Silver iodate | 7 | 0 | 0 | 0 | 0 |
| Silver iodate + CHA | 18 | 12 | 17 | 12 | 8 |
| Silver laurate + CHA | 25 | 13 | 21 | 15 | 12 |
| Silver protein | 10 | 0 | 0 | 0 | 0 |
| Silver protein + CHA | 19 | 11 | 12 | 12 | 9 |
| Silver chloride | 9 | 5 | 6 | 3 | 3 |
| Silver chloride + CHA | 18 | 11 | 17 | 13 | 13 |
| Silver oxide | 11 | 7 | 10 | 9 | 9 |
| Silver oxide + CHA | 20 | 10 | 13 | 12 | 14 |
| Silver sulfadiazine | 13 | 5 | 8 | 9 | 7 |
| Silver sulfadiazine + CHA | 16 | 11 | 15 | 14 | 13 |
| Silver tannate + CHA | 19 | — | — | — | —* |

*Experiment discontinued after 1 day because of poor quality coating.

EXAMPLE 26

I.V. catheters fabricated of Pellethane® 2363-90A were provided with coatings including a series of antimicrobial agents. A coating solution was prepared containing 6% Dow Pellethane® 2363-80AE and drug in a solvent comprising 5% N-ethyl-2-pyrrolidone (NEP) and 95% tetrahydrofuran (THF). When used alone, the Ag salt was used at a level of 5%. When combined with CHA, each was used at a level of 2%. The catheters were dipped in the solution to provide a uniform coating on the device and thereafter allowed to dry for 24 hours to remove the solvent.

1 cm segments of each catheter were soaked in TSB and incubated at 37° C. in a water bath shaker. At intervals of 0, 3, 6, 9, and 12 days, 3 segments were recovered from each group, placed in the center of blood agar plates seeded with 10 CFU of *Staph. aureus*, one section to a plate, and the zone of inhibition was measured after 24 hours at 37° C. Results, expressed as an average of 3 determinations, are given in the following Table XXII.

TABLE XXII

Antibacterial Efficacy of Drug Coated I.V. Catheters against *Staph. aureus* in Presence of Trypticase Soy Broth

| | Zone of Inhibition (mm) | | | |
|---|---|---|---|---|
| Drug on Catheter | 3 | 6 | 9 | 12 |
| Chlorhexidine (CHA) | 14 | 12 | 12 | 11 |
| Silver acetate | 9 | 9 | 9 | 9 |
| Silver acetate + CHA | 15 | 11 | 12 | 10 |
| Silver benzoate | 10 | 10 | 10 | 10 |
| Silver benzoate + CHA | 13 | 10 | 12 | 12 |
| Silver carbonate | 10 | 10 | 12 | 10 |
| Silver carbonate + CHA | 14 | 13 | 13 | 12 |
| Silver iodate | 2 | 0 | 0 | 0 |
| Silver iodate + CHA | 15 | 15 | 10 | 10 |
| Silver laurate + CHA | 26 | 15 | 15 | 15 |
| Silver protein | 8 | 0 | 0 | 0 |
| Silver protein + CRA | 15 | 12 | 15 | 15 |
| Silver palmitate + CHA | 26 | 15 | 15 | 17 |
| Silver chloride | 5 | 6 | 6 | 6 |
| Silver chloride + CHA | 20 | 13 | 13 | 14 |
| Silver oxide | 9 | 9 | 9 | 9 |
| Silver oxide + CHA | 13 | 13 | 12 | 12 |
| Silver sulfadiazine | 9 | 9 | 9 | 9 |

TABLE XXII-continued

Antibacterial Efficacy of Drug Coated
I.V. Catheters against *Staph. aureus*
in Presence of Trypticase Soy Broth

| Drug on Catheter | Zone of Inhibition (mm) | | | |
| --- | --- | --- | --- | --- |
|  | 3 | 6 | 9 | 12 |
| Silver sulfadiazine + CHA | 19 | 14 | 12 | 12 |
| Cuprous oxide | 4 | 0 | 0 | 0 |
| Cuprous oxide + CHA | 17 | 13 | 12 | 12 |

EXAMPLE 27

I.V. catheters fabricated of Pellethane® 2363-90A were provided with coatings incorporating a series of antimicrobial agents. A coating solution was prepared containing 3% Dow Pellethane® 2363-80AE and drug in a solvent comprising 5% N-ethyl-2-pyrrolidone (NEP) and 95% tetrahydrofuran (THF). The AgSD was micronized; the Ag carbonate was ground thoroughly in mortar and pestle to very fine particle size. The catheters were dipped in the solution to provide a uniform coating on the device and thereafter allowed to dry to remove the solvent.

1 cm segments of each catheter were treated and tested according to the procedure set forth in Example 26. The results obtained, expressed as maximum period of retention of activity, are given in Table XXIII below.

TABLE XXIII

Retention of Antibacterial Efficacy of
Different Drug Coated Catheters (Polyurethane I.V.)
in TSB Culture ($10^4$ *Staph. aureus*)

| Drugs in Coating Solution | Days of Activity Retained |
| --- | --- |
| None | 0 |
| AgSD (5%) | 1 |
| CHA (1%) | 3 |
| AgSD + CHA (1% + 1%) | 5 |
| Ag Carbonate + CHA (1% + 1%) | 5 |

It is to be understood that the above-described embodiments are illustrative of the application of the principles of the invention. Numerous other arrangements, processes, or compositions may be devised by those skilled in the art without departing from the spirit and scope of the invention.

We claim:

1. A method for preparing a medical article comprising forming a layer of a polymeric material containing an antiinfective agent selected from the group consisting of a biguanide and silver sulfadiazine bulk distributed therein onto a surface of a preformed hydrophilic polymeric article.

2. A method according to claim 1, wherein the polymeric material further contains an antithrombogenic agent.

* * * * *

UNITED STATES PATENT AND TRADEMARK OFFICE
CERTIFICATE OF CORRECTION

PATENT NO. : 5,616,338

DATED : April 1, 1997

INVENTOR(S) : For, Jr., et al.

It is certified that error appears in the above-identified patent and that said Letters Patent is hereby corrected as shown below:

Col. 38, line 23, "Polymeric" should read --hydrophilic polymeric--.

Signed and Sealed this

Sixteenth Day of June, 1998

Attest:

BRUCE LEHMAN

Attesting Officer

Commissioner of Patents and Trademarks